US007648990B2

(12) United States Patent
Alvaro et al.

(10) Patent No.: US 7,648,990 B2
(45) Date of Patent: *Jan. 19, 2010

(54) CHEMICAL COMPOUNDS

(75) Inventors: Giuseppe Alvaro, Verona (IT); Paola Maragni, Verona (IT); Marsia Tampieri, Verona (IT)

(73) Assignee: GlaxoSmithKline LLC, Philadelphia, PA (US)

( * ) Notice: Subject to any disclaimer, the term of this patent is extended or adjusted under 35 U.S.C. 154(b) by 127 days.

This patent is subject to a terminal disclaimer.

(21) Appl. No.: 11/865,211

(22) Filed: Oct. 1, 2007

(65) Prior Publication Data

US 2008/0021041 A1 Jan. 24, 2008

Related U.S. Application Data

(63) Continuation of application No. 11/358,631, filed on Feb. 21, 2006, now Pat. No. 7,294,630, which is a continuation of application No. 10/994,605, filed on Nov. 22, 2004, now Pat. No. 7,060,702, which is a continuation of application No. 10/398,264, filed as application No. PCT/GB01/04580 on Oct. 12, 2001, now Pat. No. 7,119,092.

(30) Foreign Application Priority Data

Oct. 17, 2000 (GB) ................................. 0025354.2

(51) Int. Cl.
*C07D 401/04* (2006.01)
*A61K 31/497* (2006.01)
(52) U.S. Cl. .................................. 514/253.13; 544/365
(58) Field of Classification Search ............. 514/253.13; 544/365
See application file for complete search history.

(56) References Cited

U.S. PATENT DOCUMENTS

| 4,087,424 A | 5/1978 | Saikawa et al. |
|---|---|---|
| 4,110,327 A | 8/1978 | Saikawa et al. |
| 4,112,090 A | 9/1978 | Saikawa et al. |
| 4,219,554 A | 8/1980 | Saikawa et al. |
| 4,308,387 A | 12/1981 | Bjork et al. |
| 4,327,097 A | 4/1982 | Saikawa et al. |
| 4,379,152 A | 4/1983 | Saikawa et al. |
| 4,410,522 A | 10/1983 | Saikawa et al. |
| 5,028,610 A | 7/1991 | Hirai et al. |
| 5,109,014 A | 4/1992 | Jacobson et al. |
| 5,334,606 A | 8/1994 | MacLeod et al. |
| 5,348,955 A | 9/1994 | Greenlee et al. |
| 5,360,820 A | 11/1994 | Hagan et al. |
| 5,464,788 A | 11/1995 | Bock et al. |
| 5,538,982 A | 7/1996 | Hagan et al. |
| 5,563,127 A | 10/1996 | Amparo et al. |
| 5,576,317 A | 11/1996 | Gonsalves et al. |
| 5,696,123 A | 12/1997 | Dollinger et al. |
| 5,698,538 A | 12/1997 | Amparo et al. |
| 5,708,006 A | 1/1998 | Dollinger et al. |
| 5,710,169 A | 1/1998 | Russell et al. |
| 5,716,942 A | 2/1998 | Dorn et al. |
| 5,756,504 A | 5/1998 | Bock et al. |
| 5,814,636 A | 9/1998 | Katano et al. |
| 5,859,015 A | 1/1999 | Graham et al. |
| 5,883,096 A | 3/1999 | Lowe et al. |
| 5,935,951 A | 8/1999 | Ofner et al. |
| 5,952,315 A | 9/1999 | Baker et al. |
| 5,977,104 A | 11/1999 | Baker et al. |
| 5,985,881 A | 11/1999 | Dollinger et al. |
| 5,998,444 A | 12/1999 | Russell et al. |
| 6,037,352 A | 3/2000 | Lowe et al. |
| 6,057,323 A | 5/2000 | Zhang et al. |
| 6,090,807 A | 7/2000 | Hellendahl et al. |
| 6,114,315 A | 9/2000 | Baker et al. |
| 6,117,855 A | 9/2000 | Carlson et al. |
| 6,147,083 A | 11/2000 | Russell et al. |
| 6,191,135 B1 | 2/2001 | Dollinger et al. |
| 6,191,139 B1 | 2/2001 | Hagan et al. |
| 6,197,772 B1 | 3/2001 | Janssens et al. |
| 6,235,732 B1 | 5/2001 | Dollinger et al. |
| 6,288,068 B1 | 9/2001 | Lowe et al. |
| 6,319,953 B1 | 11/2001 | Carlson et al. |
| RE37,886 E | 10/2002 | Janssens et al. |
| 6,521,621 B1 | 2/2003 | Janssens et al. |
| 6,642,240 B2 | 11/2003 | Alvaro et al. |
| 7,060,702 B2 * | 6/2006 | Alvaro et al. ........... 514/253.13 |
| 7,119,092 B2 * | 10/2006 | Alvaro et al. ........... 514/253.13 |
| 7,294,630 B2 * | 11/2007 | Alvaro ................... 514/253.13 |
| 2002/0103205 A1 | 8/2002 | Lowe et al. |

FOREIGN PATENT DOCUMENTS

| DE | 2519400 | 4/1978 |
|---|---|---|
| EP | 287734 | 10/1987 |

(Continued)

OTHER PUBLICATIONS

European Search Report for Application No. 08151841.7-2117. 7 pages.

(Continued)

*Primary Examiner*—Peter G O'Sullivan
(74) *Attorney, Agent, or Firm*—J. Scott Young

(57) ABSTRACT

The present invention provides a method for the treatment of emesis in a mammal being treated with an opiod analgesic.

67 Claims, No Drawings

FOREIGN PATENT DOCUMENTS

| | | |
|---|---|---|
| EP | 293532 | 10/1987 |
| EP | 0655442 | 5/1995 |
| EP | 718287 | 12/1995 |
| EP | 0721941 | 7/1996 |
| EP | 0655422 | 5/2001 |
| GB | 1508062 | 4/1975 |
| JP | 57/118587 | 7/1982 |
| WO | WO 92/16211 | 10/1992 |
| WO | WO 95/00498 | 1/1995 |
| WO | WO 95/25443 | 9/1995 |
| WO | WO 96/02503 | 2/1996 |
| WO | WO 96/03378 | 2/1996 |
| WO | WO 96/10562 | 4/1996 |
| WO | WO 96/14844 | 5/1996 |
| WO | WO 96/20173 | 7/1996 |
| WO | WO 97/16440 | 5/1997 |
| WO | WO 97/32865 | 9/1997 |
| WO | WO 97/36592 | 10/1997 |
| WO | WO 97/36593 | 10/1997 |
| WO | WO 97/36888 | 10/1997 |
| WO | WO 97/36889 | 10/1997 |
| WO | WO 98/01133 | 1/1998 |
| WO | WO 98/20001 | 5/1998 |
| WO | WO 98/57954 | 12/1998 |
| WO | WO 99/09985 | 3/1999 |
| WO | WO 99/26921 | 6/1999 |
| WO | WO 01/25219 | 4/2001 |
| WO | WO 02/32867 | 4/2002 |
| WO | WO 02/057233 | 7/2002 |
| WO | WO 2004/033428 | 4/2004 |

OTHER PUBLICATIONS

DeWinter, B.Y., et al. "Effect Of Different Prokinetic Agents and a Novel Enterokinetic Agent on Postoperative Ileus in Rats." GUT, British Medical Association, London, GB., vol. 45, No. 5, 1999, pp. 713-718.

Megens, A., et al. J. Pharmacology and Experimental Therapeutics (2002 302(2):696-709.

Chattel, E., et al. Neuropharmacology (2001) 40(3): 408-415.

Romerio, el al., Clinical Pharmacology and Therapeutics (1999) 66(5):522-527.

Rupniak, et al. "Differential inhibition of foot tapping and chromodacryorrhea in gerbils by CNS penetrant And non-penetrant tachykinin NK 1 receptor antagonists," European Journal of Pharmacology 265: 179-183 (1994).

Davis, David T., "Synthesis A. Biological Activity of a Series of Piperazin-2,3-Diones," Journal of Antibiotics, vol. XLII, No. 3, 1989, pp. 367-373.

Pacher, P., et al. "Review of Cardiovascular Effects of Fluoxetine, A Selective Serotonine Reuptake Inhibitor, Compared to Tricyclic Antidepressants." Current Medicinal Chemistry, 1998, 5, 381-390.

* cited by examiner

CHEMICAL COMPOUNDS

CROSS REFERENCES TO RELATED APPLICATIONS

This application is a continuation of U.S. patent application Ser. No. 11/358,631, filed 21 Feb. 2006, now U.S. Pat. No. 7,294,630, granted 13 Nov. 2007; which is a continuation of U.S. patent application Ser. No. 10/994,605, filed 22 Nov. 2004, now U.S. Pat. No. 7,060,702 granted 13 Jun. 2006; which is a continuation of U.S. patent application Ser. No. 10/398,264, having a 371 (c)(1), (2), (4) date of 29 Jul. 2003, now U.S. Pat. No. 7,119,092, granted 10 Oct. 2006; which is a 371 Application of PCT/GB01/04580, filed 12 Oct. 2001; which claims priority to GB Application Serial No. 0025354.2, filed 17 Oct. 2000.

BACKGROUND OF THE INVENTION

The present invention relates to piperidine derivatives, to processes for their preparation, to pharmaceutical compositions containing them and to their medical use.

In particular the invention relates to novel compounds which are potent and specific antagonists of tachykinins, including substance P and other neurokinins.

WO 97/16440 describes 1-(1,2-disubstituted piperidinyl)-4-substituted piperazine derivatives of general formula

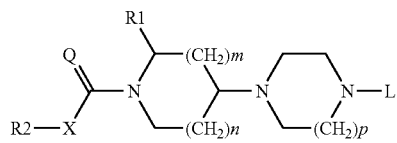

wherein n and m are inter alia 1, p is 1; Q is inter alia oxygen; X is a covalent bond or a bivalent radical of formula —O—, —S—, NR$^3$; R$^3$ is hydrogen or a C$_{1-6}$ alkyl group; R$^1$ is inter alia Ar$^1$; R$^2$ may be inter alia Ar$^2$C$_{1-6}$alkyl wherein Ar$^2$ and Ar$^1$ are inter alia a phenyl group which may be substituted with 1, 2 or 3 substituents each independently selected from halo, C$_{1-4}$alkyl, haloC$_{1-4}$ alkyl, L may be inter alia hydrogen, C$_{1-6}$ alkyl or L is a radical of formula —(CHR$^4$)rC(O)Y$^1$R$^7$, wherein r is 0, 1, 2, 3 or 4, Y$^1$ is inter alia a NH or a N(C$_{1-6}$ alkyl) group or Y$^1$ is a covalent bond and R$^7$ is inter alia C$_{1-6}$ alkyl or C$_{3-7}$ cycloalkyl. The compounds are antagonists of tachykinins.

We have now found a particular class of compounds which is not specifically disclosed therein, which class has special advantages.

We have discovered that by selection of particular substituents (namely a piperazin-1-yl substituent at the 4-position of the piperidine ring, substituted phenyl alkyl amide groups at the 1-position and substituted phenyl groups at the 2-position) a class of compounds having advantageous properties in the treatment of conditions mediated by tachykinins is obtained.

DETAILED DESCRIPTION OF THE INVENTION

Thus the present invention provides compounds of formula (I)

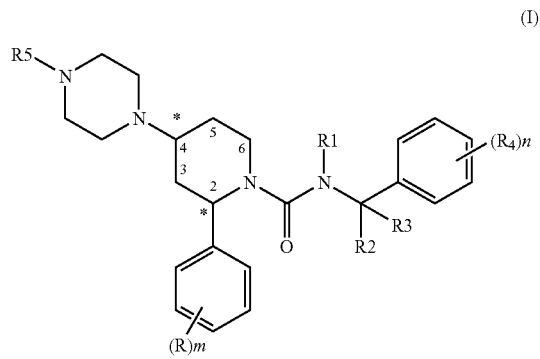

wherein
R represents a halogen atom or a C$_{1-4}$ alkyl group;
R$_1$ represents a C$_{1-4}$ alkyl group;
R$_2$ represents hydrogen or a C$_{1-4}$ alkyl group;
R$_3$ represents hydrogen, or a C$_{1-4}$ alkyl group;
R$_4$ represents a trifluoromethyl group;
R$_5$ represents hydrogen, a C$_{1-4}$ alkyl group or C(O)R$_6$;
R$_6$ represents C$_{1-4}$ alkyl, C$_{3-7}$ cycloalkyl, NH(C$_{1-4}$ alkyl) or N(C1-4alkyl)$_2$;
m is zero or an integer from 1 to 3;
n is an integer from 1 to 3;
and pharmaceutically acceptable salts and solvates thereof.

A further embodiment of the invention provides compounds of formula (I) and pharmaceutically acceptable salts and solvates thereof, wherein
R represents a halogen atom or a C$_{1-4}$ alkyl group;
R$_1$ represents a C$_{1-4}$ alkyl group;
R$_2$ represents hydrogen or a C$_{1-4}$ alkyl group;
R$_3$ represents hydrogen or a C$_{1-4}$ alkyl group;
R$_4$ represents a trifluoromethyl group;
R$_5$ represents hydrogen, a C$_{1-4}$ alkyl group or C(O)R$_6$;
R$_6$ represents C$_{1-4}$ alkyl;
m is zero or an integer from 1 to 3;
n is an integer from 1 to 3.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The solvates may, for example, be hydrates.

References hereinafter to a compound according to the invention include both compounds of formula (I) and their pharmaceutically acceptable acid addition salts together with pharmaceutically acceptable solvates.

Suitable pharmaceutical acceptable salts of the compounds of general formula (I) may be obtained in a crystalline form and/or in an amorphous form or as a mixture thereof.

It will be appreciated by those skilled in the art that the compounds of formula (I) contain at least two chiral centres (namely the carbon atoms shown as * in formula (I)) and these may be represented by the formulae (1a, 1b, 1c and 1d).

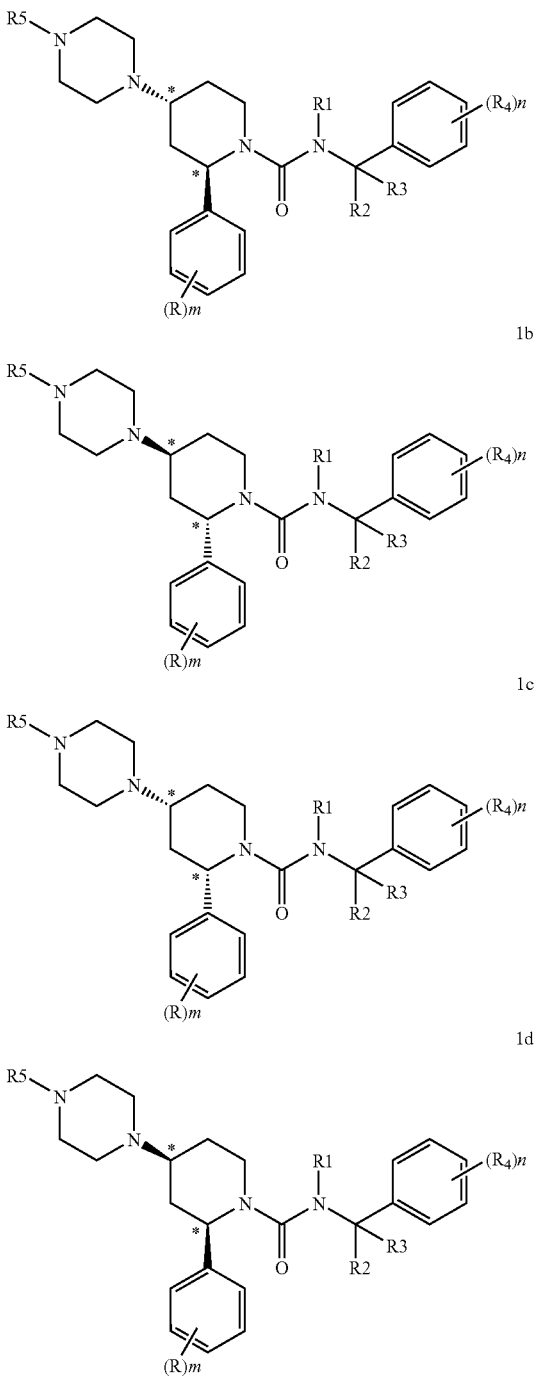

The wedge shaped bond indicates that the bond is above the plane of the paper and is referred to as β configuration. The broken bond indicates that the bond is below the plane of the paper and is in the α configuration.

In general, in the specific compounds named below the β configuration at the 2 position corresponds to the R configuration and the β configuration at 4 position corresponds to the S configuration. The α configuration at the 2 position corresponds to the S configuration and the α configuration at 4 position corresponds to the R configuration. The assignment of the R or S configuration at the 2 and the 4 positions have been made according to the rules of Cahn, Ingold and Prelog, Experientia 1956, 12, 81.

The configuration of the chiral carbons atom of the piperidine ring shown in 1a and 1b is hereinafter referred to as anti configuration and in formulae 1c and 1d as the syn configuration.

Further asymmetric carbon atoms are possible in the compound of formula (I). Thus, when $R_2$ and $R_3$ are not the same group, the compounds of formula (I) possess at least three asymmetric carbon atoms.

It is to be understood that all enantiomers and diastereoisomers and mixtures thereof are encompassed within the scope of the present invention.

The term alkyl as used herein as a group or a part of the group refers to a straight or branched alkyl group containing from 1 to 4 carbon atoms; examples of such groups include methyl, ethyl, propyl, isopropyl, n-butyl, isobutyl or tert butyl.

The term halogen refers to a fluorine, chlorine, bromine or iodine atom.

The term $C_{3-7}$ cycloalkyl group means a non-aromatic monocyclic hydrocarbon ring of 3 to 7 carbon atom such as, for example, cyclopropyl, cyclobutyl, cyclopentyl, cyclohexyl or cycloheptyl.

A preferred group of compounds of formula (I) are those in which the carbon atom at the 2-position of piperidine ring is in the β configuration. Within this group, those compounds in which the carbon atom at the 4-position is in the β configuration are particularly preferred.

When R represents halogen this is suitably chlorine or more preferably fluorine or when R is $C_{1-4}$ alkyl this is suitably methyl or ethyl wherein m is zero or an integer from 1 to 2.

Suitable values for $R_2$ or $R_3$ include hydrogen, a methyl, an ethyl or a propyl group.

R is preferably a halogen (e.g. fluorine) and/or a $C_{1-4}$ alkyl (e.g. methyl) group and m is preferably zero or an integer from 1 to 2.

$R_1$ is preferably a methyl group.

$R_2$ is preferably a hydrogen atom or a methyl group.

$R_3$ is preferably a hydrogen atom or a methyl group.

$R_5$ is preferably a hydrogen atom, methyl, isopropyl or a C(O)cyclopropyl, a C(O)CH$_3$, a C(O)NHCH$_3$ or a C(O)N(CH$_3$)$_2$ group.

A preferred class of compounds of formula (I) are those wherein each R is independently a halogen (e.g. fluorine) or a $C_{1-4}$ alkyl (e.g. methyl) group, wherein m is 0, 1 or 2. More preferably m is 1 or 2. Within this class those wherein R is at the 2 and/or 4 position in the phenyl ring are particularly preferred.

Compounds of formula (I), wherein n is 2, represent a preferred class of compounds and within this class the groups $R_4$ are preferably at the 3 and 5 position in the phenyl ring.

A further preferred class of compounds of formula (I) is that wherein $R_1$ is methyl, $R_2$ or $R_3$ represent independently hydrogen or a methyl group.

A particularly preferred group of compounds of formula (I) is that wherein each R is independently halogen or methyl at the 2 and/or 4 position, the groups $R_4$ are at the 3 and 5 position, $R_1$ is methyl, $R_2$ and $R_3$ are independently hydrogen or methyl and $R_5$ is methyl, isopropyl or a C(O)cyclopropyl, a C(O)CH$_3$, a C(O)NHCH$_3$ or a C(O)N(CH$_3$)$_2$ group, m is 1 or 2 and n is 2.

Preferred compounds according to the invention are:

4-(R)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;

4-(S)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide;

4-(R)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide;

2-(R)-(4-Fluoro-2-methyl-phenyl)-4-(R,S)-(4-methyl-piperazin-1-yl)-piperidine-1-carboxylic acid, [1-(R)-(3,5-bis-trifluoromethyl-phenyl)-ethyl]-methylamide;

2-(R)-(4-Fluoro-2-methyl-phenyl)-4-(S)-piperazin-1-yl-piperidine-1-carboxylic acid, [1-(R)-(3,5-bis-trifluoromethyl-phenyl)-ethyl]-methylamide;

2-(R)-(4-Fluoro-2-methyl-phenyl)-4-(R,S)-(4-methyl-piperazin-1-yl)-piperidine-1-carboxylic acid, (3,5-bis-trifluoromethyl-benzyl)-methylamide;

4-(S)-(4-Cyclopropanoyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;

4-(R)-(4-Cyclopropanoyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;

4-(S)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide;

4-(R)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide;

4-(S)-[1-[(3,5-Bis-trifluoromethyl-benzyl)-methyl-carbamoyl]-2-(R)-(4-fluoro-2-methyl-phenyl)-piperidin-4-yl]-piperazine-1-carboxylic acid, dimethylamide;

4-(S)-[1-[(3,5-Bis-trifluoromethyl-benzyl)-methyl-carbamoyl]-2-(R)-(4-fluoro-2-methyl-phenyl)-piperidin-4-yl]-1-carboxylic acid, methylamide;

4-(S)-[1-[(3,5-Bis-trifluoromethyl-benzyl)-methyl-carbamoyl]-2-(R)-(4-fluoro-2-methyl-phenyl)-piperidin-4-yl]-piperazine;

4-(S)-(4-Acetyl-piperazin-1-yl)-2-(R)-(4-fluoro-phenyl)-piperidine-1-carboxylic acid, [1-(R)-(3,5-bis-trifluoromethyl-phenyl)-ethyl]-methylamide;

4-(R)-(4-Acetyl-piperazin-1-yl)-2-(R)-(4-fluoro-phenyl)-piperidine-1-carboxylic acid, [1-(R)-(3,5-bis-trifluoromethyl-phenyl)-ethyl]-methylamide;

and pharmaceutically acceptable salts (e.g. hydrochloride, methanesulphonate, sulphate, p-toluenesulphonate) or solvates thereof.

Further preferred compounds of the invention are:

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide methanesulphonate;

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide sulfate;

4-(S)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide hydrochloride.

Particularly preferred compound of the invention is 4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide methanesulphonate;

The compounds of the invention are antagonists of tachykinins, including substance P and other neurokinins, both in vitro and in vivo and are thus of use in the treatment of conditions mediated by tachykinins, including substance P and other neurokinins.

$NK_1$-receptor binding affinity has been determined in vitro by the compounds' ability to displace [3H]-substance P (SP) from recombinant human $NK_1$ receptors expressed in Chinese Hamster Ovary (CHO) cell membranes.

CHO cell membranes were prepared by using a modification of the method described by Dam T and Quirion R (Peptides, 7:855-864, 1986). Thus ligand binding was performed in 0.4 ml of 50 mM HEPES, pH 7.4, containing 3 mM $MnCl_2$, 0.02% BSA, 0.5 nM [$^3$H]Substance P (30÷56 Ci/mmol, Amersham), a final membrane concentration of 25 μg of protein/ml, and the test compounds. The incubation proceeded at room temperature for 40 min. Non-specific binding was determined using excess of Substance P (1 μM) and represents about 6% of the total binding.

Compounds of the invention were further characterised in a functional assay for the determination of their inhibitory effect. Human-$NK_1$-CHO cells were stimulated with Substance P and the receptor activation was evaluated by measuring the accumulation of cytidinediphosphodiacylglycerol (CDP-DAG), which is the liponucleotide precursor of phosphatidylinositol diphosphate. CDP-DAG accumulates in the presence of $Li^+$ as a consequence of the receptor mediated activation of phospholipase C (PLC) (Godfrey, Biochem. J., 258:621-624, 1989). The method is described in detail by Ferraguti et al. (Mol. Cell. Neurosci., 5:269-276, 1994).

The action of the compounds of the invention at the $NK_1$ receptor may be determined by using conventional tests. Thus the ability to penetrate the central nervous system and to bind at the $NK_1$ receptor was demonstrated in vivo by their inhibitory effect on the change in the behaviour induced by intracerebroventricular applied substance P in the gerbil, according to the gerbil foot tapping model as described by Rupniak & Williams, Eur. J. of Pharmacol., 1994.

Compounds of the invention are useful in the treatment of CNS disorders. In particular they are useful in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention have also been found to exhibit anxiolytic activity in conventional tests. For example in marmoset human threat test (Costall et al., 1988).

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful in the treatment of sleep disorders including dysomnia, insomnia, sleep apnea, narcolepsy, and circadian ritmic disorders.

Compounds of the invention are also useful in the treatment or prevention of the cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g cannabis, heroin, morphine) or benzodiazepines; in the treatment of cocaine, sedative ipnotic, amphetamine or amphetamine-related drugs (e.g dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are of particular use in the treatment of depressive states, in the treatment of anxiety and of panic disorders. Depressive states include major depressive disorders including bipolar depression, unipolar depression, single or recurrent major depressive episodes with or without psychotic features, catatonic features, melancholic features, atypical features or postpartum onset, dysthymic disorder with early or late onset and with or without atypical features, neurotic depression and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type.

Compounds of the invention may be administered in combination with other active substances such as 5HT3 antagonists, serotonin agonists, selective serotonin reuptake inhibitors (SSRI), noradrenaline re-uptake inhibitors (SNRI), tricyclic antidepressants or dopaminergic antidepressants.

Suitable 5HT3 antagonists which may be used in combination of the compounds of the inventions include for example ondansetron, granisetron and metoclopramide.

Suitable serotonin agonists which may be used in combination with the compounds of the invention include sumatriptan, rauwolscine, yohimbine and metoclopramide.

Suitable SSRI which may be used in combination with the compounds of the invention include fluoxetine, citalopram, femoxetine, fluvoxamine, paroxetine, indalpine, sertraline and zimeldine.

Suitable SNRI which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of the combination or composition may be administered simultaneously (either in the same or different pharmaceutical formulations) or sequentially.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Compounds of formula (I), and salts and solvates thereof, may be prepared by the general methods outlined hereinafter. In the following description, the groups R, $R_1$, $R_2$, $R_3$, $R_4$, $R_5$, $R_6$ m and n, have the meaning as previously defined for compounds of formula (I) unless otherwise stated.

Compounds of formula (I) may be prepared by reductive N-alkylation of a compound of formula (II),

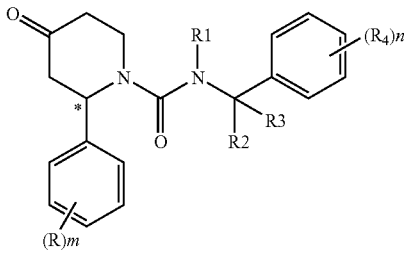

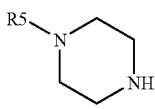

with a piperazine derivative (III) in an aprotic solvent such as dichloroethane and in the presence of a suitable metal reducing agent such as sodium borohydride or sodium triacetoxyborohydride.

Compounds of formula (II) may be prepared by treating compounds of formula (IV)

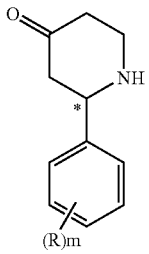

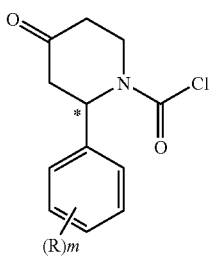

with triphosgene in an aprotic solvent such as dichloromethane and in the presence of an organic base such triethylamine to form the intermediate carbonyl chloride compound (V) which may be isolated if required, followed by reaction of compound (V) with the amine compound (VI)

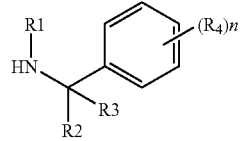

The reaction conveniently takes place in an aprotic solvent such as a hydrocarbon, a halohydrocarbon such as dichloromethane or an ether such as tetrahydrofuran optionally in the presence of a base such as a tertiary amine e.g. diisopropylethylamine.

Where it is desired to isolate a compound formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compounds of formula (I) using conventional methods.

Compounds of formula (III), (IV), (V) and (VI) may be prepared by analogous methods to those used for known compounds.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, for example, specific enantiomers of the compounds of formula (I) may be obtained from the corresponding enantiomeric mixture of a compound of formula (I) using chiral HPLC procedure.

Alternatively, enantiomers of a compound of general formula (I) may be synthesised from the appropriate optically active intermediates using any of the general processes described herein.

Thus for example the required enantiomer may be prepared by the corresponding a chiral piperidin-4-one of formula (IV) using the process described above for preparing compounds of formula (I) from compounds (IV)., followed by separation of the diastereomeric mixture of a compound of formula (I) using conventional procedure.

The chiral compounds (IV) may be prepared from the corresponding racemic compound (IV) using conventional procedures such as salt formation with a suitable optically active acid, separating the resultant diastereoisomeric salts by conventional means e.g. chromatography and crystallisation followed by hydrolysis of the diastereoisomeric salts.

A suitable optically active acid for use in the process is L(+)mandelic acid.

In a further embodiment of the invention the chiral compound (IV) may be prepared using Comins reaction as described in Journal American Chemical Society 1994, 116, 4719-4728, followed by reduction of 2,3 dihydro-1H-pyridin-4-one derivative to piperidin-4-one derivative. The reduction may be effected using hydrogen and metal catalyst e.g.

palladium on a suitable support e.g. carbon or alumina. The reaction is carried out in a solvent such as ester e.g. ethyl acetate.

In a further embodiment of the invention the enantiomers of the compound of formula (I) may be prepared by reaction of a chiral amine (VI) using any of the processes described above for preparing compounds of formula (I) from amine (V).

The chiral amine (III) may be prepared from the corresponding racemic amine (III) using any conventional procedures such as salt formation with a suitable optically active acid.

The invention is further illustrated by the following Intermediates and Examples which are not intended as a limitation of the invention.

In the Intermediates and Examples unless otherwise stated:

Melting points (m.p.) were determined on a Buchi m.p. apparatus and are uncorrected. R.T. or r.t. refer to room temperature.

Infrared spectra (IR) were measures in chloroform or nujol solutions on a FT-IR instrument. Proton Magnetic Resonance (NMR) spectra were recorded on Varian instruments at 400 or 500 MHz, chemical shifts are reported in ppm (δ) using the residual solvent line as internal standard. Splitting patterns are designed as s, singlet; d, double; t, triple; q, quartet; m, multiplet; b, broad. Mass spectra (MS) were taken on a VG Quattro mass spectrometer. Optical rotations were determined at 20° C. with a Jasco DIP360 instrument (l=10 cm, cell volume=1 mL, λ=589 nm). Flash silica gel chromatography was carried out over silica gel 230-400 mesh supplied by Merck AG Darmstadt, Germany. T.l.c. refers to thin layer chromatography on 0.25 mm silica gel plates (60F-254 Merck) and visualized with UV light.

Solutions were dried over anhydrous sodium sulphate.

Methylene chloride was redistilled over calcium hydride and tetrahydrofuran was redistilled over sodium.

The following abbreviation are used in the text: AcOEt=ethyl acetate, CH=cyclohexane, DCM=methylene chloride, DIPEA=N,N-diisopropylethylamine, DMF=N,N'-dimethylformamide, Et2O=diethyl ether, EtOH=ethanol, MeOH=methanol, TEA=triethylamine, THF=tetrahydrofuran.

INTERMEDIATE 1

1-(Benzyloxycarbonyl)-2-(4-fluoro-2-methyl-phenyl)-2,3-dihydro-4-pyridone

A small amount of iodine was added to a suspension of magnesium turnings (13.2 g) in dry THF (300 mL), at r.t., under a nitrogen atmosphere, then the mixture was vigorously refluxed for 20 minutes. To this suspension, a 15% of a solution of 2-bromo-5-fluoro-toluene (52.5 mL) in anhydrous THF (300 mL) was added. The suspension was heated under vigorous reflux until the brown colour disappeared. The remaining part of the bromide solution was added drop-wise over 1 hour to the refluxing suspension which was then stirred for a further 1 hour. This solution of Grignard reagent was then added drop-wise to the pyridinium salt obtained from benzyl chloroformate (48.7 mL) and 4-methoxypyridine (25 mL) in dry THF (900 mL) at −23° C.

The obtained solution was stirred 1 hour at −20° C. then it was warmed up to 20° C., a 10% hydrochloric acid solution (560 mL) was added and the aqueous layer was extracted with AcOEt (2×750 mL).

The combined organic extracts were washed with 5% sodium hydrogen carbonate solution (600 mL) and brine (600 mL) then partially concentrated in vacuo.

CH (400 mL) was added drop-wise over 1 hour at 20° C. and the resulting mixture was stirred 30 minutes and then filtered to give the title compound as a white solid (66 g).

IR (nujol, cm$^{-1}$): 1726 and 1655 (C=O), 1608 (C=C).

NMR (d$_6$-DMSO): δ (ppm) 8.19 (d, 1H); 7.31-7.18 (m, 5H); 7.08 (m, 2H); 6.94 (dt, 1H); 5.77 (d, 1H); 5.36 (d, 1H); 5.16 (2d, 2H); 3.26 (dd, 1H); 2.32 (d, 1H); 2.26 (s, 3H).

MS (ES/+): m/z=340 [MH]$^+$.

INTERMEDIATE 2

2-(4-Fluoro-2-methyl-phenyl)-piperidine-4-one

Method A

2-Methyl-4-fluoro-benzaldehyde (4 g) was added to a solution of 4-aminobutan-2-one ethylene acetal (3.8 g) in dry benzene (50 mL) and the solution was stirred at r.t. under a nitrogen atmosphere. After 1 hour the mixture was heated at reflux for 16 hours and then allowed to cool to r.t. This solution was slowly added to a refluxing solution of p-toluensulphonic acid (10.6 g) in dry benzene (50 mL) previously refluxed for 1 hour with a Dean-Stark apparatus. After 3.5 hours the crude solution was cooled and made basic with a saturated potassium carbonate solution and taken up with AcOEt (50 mL). The aqueous phase was extracted with AcOEt (3×50 mL) and Et2O (2×50 mL). The organic layer was dried and concentrated in vacuo to a yellow thick oil as residue (7.23 g). A portion of the crude mixture (3 g) was dissolved in a 6N hydrochloric acid solution (20 mL) and stirred at 60° C. for 16 hours. The solution was basified with solid potassium carbonate and extracted with DCM (5×50 mL). The combined organic phases were washed with brine (50 mL), dried and concentrated in vacuo to give the title compound (2.5 g) as a thick yellow oil.

Method B

L-selectride (1M solution in dry THF, 210 mL) was added drop-wise, over 80 minutes, to a solution of intermediate 1 (50 g) in dry THF (1065 mL) previously cooled to −72° C. under a nitrogen atmosphere. After 45 minutes, 2% sodium hydrogen carbonate solution (994 mL) was added drop-wise and the solution was extracted with AcOEt (3×994 mL). The combined organic phases were washed with water (284 mL) and brine (568 mL). The organic phase was dried and concentrated in vacuo to get 1-benzyloxycarbonyl-2-(4-fluoro-2-methyl-phenyl)-piperidine-4-one as a pale yellow thick oil (94 g) which was used as a crude.

This material (94 g) was dissolved in AcOEt (710 mL), then 10% Pd/C (30.5 g) was added under a nitrogen atmosphere. The slurry was hydrogenated at 1 atmosphere for 30 minutes. The mixture was filtered through Celite and the organic phase was concentrated in vacuo to give the crude 2-(4-fluoro-2-methyl-phenyl)-piperidine-4-one as a yellow oil. This material was dissolved in AcOEt (518 mL) at r.t. and racemic camphorsulphonic acid (48.3 g) was added. The mixture was stirred at r.t for 18 hours, then the solid was filtered off, washed with AcOEt (2×50 mL) and dried in vacuo for 18 hours to give 2-(4-fluoro-2-methyl-phenyl)-piperidine-4-one, 10-camphorsulfonic acid salt as a pale yellow solid (68.5 g). (M.p.: 167-169° C.—

NMR (d$_6$-DMSO): δ (ppm) 9.43 (bs, 1H); 9.23 (bs, 1H); 7.66 (dd, 1H); 7.19 (m, 2H); 4.97 (bd, 1H); 3.6 (m, 2H); 2.87

(m, 3H); 2.66 (m, 1H); 2.53 (m, 2H); 2.37 (s+d, 4H); 2.22 (m, 1H); 1.93 (t, 1H); 1.8 (m, 2H); 1.26 (m, 2H); 1.03 (s, 3H); 0.73 (s, 3H).

This material (68.5 g) was suspended in AcOEt (480 mL) and stirred with a saturated sodium hydrogen carbonate (274 mL). The organic layer was separated and washed with further water (274 mL). The organic phase was dried and concentrated in vacuo to give the title compound (31 g) as a yellow-orange oil.

NMR ($d_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).

MS (ES/+): m/z=208 $[MH]^+$.

INTERMEDIATE 3

2-(4-Fluoro-2-methyl-phenyl)-4-oxo-piperidine-1-carboxylic acid, (3,5-bis-trifluoromethyl-benzyl)-methylamide A solution of triphosgene (1.43 g) dissolved in dry DCM (10 mL) was added to a solution of intermediate 2 (2.5 g) and DIPEA (8.4 mL) in dry DCM (20 mL) previously cooled to 0° C. under a nitrogen atmosphere. The solution was stirred at 0° C. for 2 hours, then (3,5-bis-trifluoromethyl-benzyl)-methylamine hydrochloride (5.63 g) and DIPEA (3.34 mL) were added. The mixture was stirred under nitrogen at r. t. for 14 hours. The mixture was taken up with AcOEt (50 mL), washed with cold 1N hydrochloric acid solution (3×20 mL) and brine (10 mL). The organic layer was dried and concentrated in vacuo to a residue which was purified by flash chromatography (AcOEt/CH 3:7) to give the title compound as a white foam (3.85 g).

IR (nujol, $cm^{-1}$): 1721 and 1641 (C=O).

NMR ($d_6$-DMSO): δ (ppm) 7.96 (s, 1H); 7.76 (s, 2H); 7.25 (dd, 1H); 6.97 (dd, 1H); 6.90 (dt, 1H); 5.22 (t, 1H); 4.59 (d, 1H); 4.43 (d, 1H); 3.63-3.49 (m, 2H); 2.79 (s, 3H); 2.69 (m, 2H); 2.49 (m, 2H); 2.26 (s, 3H).

MS (ES/+): m/z=491 $[MH]^+$.

INTERMEDIATE 4

2-(R)-(4-Fluoro-2-methyl-phenyl)-4-oxo-piperidine-1-carboxylic acid, [1-(R)-3,5-bis-trifluoromethyl-phenyl)-ethyl]-methylamide (4a) and 2-(S)-(4-Fluoro-2-methyl-phenyl)-4-oxo-piperidine-1-carboxylic acid, [1-(R)-3,5-bis-trifluoromethyl-phenyl)-ethyl]-methylamide (4b)

Method A

A solution of triphosgene (147 mg) dissolved in dry DCM (5 mL) was added drop-wise to a solution of intermediate 2 (250 mg) and DIPEA (860 μL) in dry DCM (15 mL) previously cooled to 0° C. under a nitrogen atmosphere. After 2 hours, [1-(R)-3,5-bis-trifluoromethyl-phenyl)-ethyl]-methylamine hydrochloride (503 mg) and DIPEA (320 μL) in dry acetonitrile (20 mL) were added and the mixture was heated to 70° C. for 16 hours. Further [1-(R)-(3,5-bis-trifluoromethyl-phenyl)-ethyl]-methylamine hydrochloride (170 mg) and DIPEA (100 μL) were added and the mixture was stirred at 70° C. for further 4 hours. Next, the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 4a (230 mg) as a white foam,
2. intermediate 4b (231 mg) as a white foam.

INTERMEDIATE 4a

NMR ($d_6$-DMSO): δ (ppm) 7.98 (bs, 1H); 7.77 (bs, 2H); 7.24 (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

INTERMEDIATE 4b

NMR ($d_6$-DMSO): δ (ppm) 7.96 (bs, 1H); 7.75 (bs, 2H); 7.24 (dd, 1H); 6.98 (dd, 1H); 6.93 (dt, 1H); 5.29 (q, 1H); 5.24 (t, 1H); 3.56 (m, 1H); 3.48 (m, 1H); 2.70 (s, 3H); 2.50 (m, 4H); 2.26 (s, 3H); 1.54 (d, 3H).

INTERMEDIATE 4a

Method B

A saturated sodium hydrogen carbonate solution (324 mL) was added to a solution of intermediate 9 (21.6 g) in AcOEt (324 mL) and the resulting mixture was vigorously stirred for 15 minutes. The aqueous layer was back-extracted with further AcOEt (216 mL) and the combined organic extracts were dried and concentrated in vacuo to give intermediate 8 as a yellow oil, which was treated with TEA (19 mL) and AcOEt (114 mL). The solution obtained was added drop-wise over 40 minutes to a solution of triphosgene (8 g) in AcOEt (64 mL) previously cooled to 0° C. under a nitrogen atmosphere, maintaining the temperature between 0° C. and 8° C.

After stirring for 1 hours at 0° C. and for 3 hours at 20° C., [1-(R)-(3,5-bis-trifluoromethyl-phenyl)-ethyl]-methylamine hydrochloride (29.7 g), AcOEt (190 mL) and TEA (38 mL) were added to the reaction mixture which was then heated to reflux for 16 hours.

The solution was washed with 10% sodium hydroxide solution (180 mL), 1% hydrochloric acid solution (4×150 mL), water (3×180 mL) and brine (180 mL). The organic layer was dried and concentrated in vacuo to a residue, which was purified through a silica pad (CH/AcOEt 9:1) to give the title compound (21.5 g) as a brown thick oil.

NMR ($d_6$-DMSO): δ (ppm) 7.97-7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

INTERMEDIATE 5

2-(S)-(4-Fluoro-2-methyl-phenyl)-4-oxo-piperidine-1-carboxylic acid, [1-(S)-(3,5-bis-trifluoromethyl-phenyl)-ethyl]-methylamide (5a) and 2-(R)-(4-Fluoro-2-methyl-phenyl)-4-oxo-piperidine-1-carboxylic acid, [1-(S)-(3,5-bis-trifluoromethyl-phenyl)-ethyl]-methylamide (5b)

A solution of triphosgene (147 mg) dissolved in dry DCM (5 mL) was added to a solution of intermediate 2 (250 mg) and DIPEA (860 μL) in dry DCM (15 mL) previously cooled to 0° C. under a nitrogen atmosphere. After 2 hours, a solution of [1-(S)-(3,5-bis-trifluoromethyl-phenyl)-ethyl]-methylamine hydrochloride (510 mg) and DIPEA (320 μL) in dry acetonitrile (20 mL) was added and the mixture was heated to 70° C. for 16 hour. Next, further [1-(S)-(3,5-bis-trifluoromethyl-phenyl)-ethyl]-methylamine hydrochloride (170 mg) and DIPEA (105 μL) were added. After further 4 hours at 70° C., the mixture was allowed to cool to r.t., taken up with AcOEt (30 mL), washed with a 1N hydrochloric acid cold solution (3×15 mL) and brine (2×10 mL). The organic layer was dried and concentrated in vacuo to a residue, which was purified by flash chromatography (CH/AcOEt 8:2) to give:
1. intermediate 5a (234 mg) as a white foam,
2. intermediate 5b (244 mg) as a white foam.

INTERMEDIATE 5a

NMR ($d_6$-DMSO): δ (ppm) 7.97-7.77 (bs+bs, 3H); 7.24 (dd, 1H); 6.97 (dd, 1H); 6.88 (td, 1H); 5.24 (m, 1H); 5.14 (q, 1H); 3.58 (m, 2H); 2.7 (m, 2H); 2.56 (s, 3H); 2.49 (m, 2H); 2.26 (s, 3H); 1.57 (d, 3H).

INTERMEDIATE 5b

NMR ($d_6$-DMSO): δ (ppm) 7.98 (bs, 1H); 7.77 (bs, 2H) 7.24° (dd, 1H); 6.97 (dd, 1H); 6.89 (m, 1H); 5.24 (t, 1H); 5.14 (q, 1H); 3.61 (m, 1H); 3.55 (m, 1H); 2.71 (m, 2H); 2.56 (s, 3H); 2.50 (m, 2H); 2.26 (s, 3H); 1.57 (d, 3H).

INTERMEDIATE 6

2-(S)-(4-Fluoro-2-methyl-phenyl)-4-oxo-3,4-dihydro-2H-pyridine-1-carboxylic acid, (1R,2S,5R)-2-isopropyl-5-methyl-cyclohexyl ester (6a) and 2-(R)-(4-Fluoro-2-methyl-phenyl)-4-oxo-3,4-dihydro-2H-pyridine-1-carboxylic acid, (1R,2S,5R)-2-isopropyl-5-methyl-cyclohexyl ester (6b)

A solution of 2-bromo-5-fluoro-toluene (3.68 g) in dry THF (10 mL) was dropped over 30 minutes, into a mixture of magnesium (525 mg) and iodine (1 crystal) in dry THF (5 mL) previously heated to 70° C. under a nitrogen atmosphere. The mixture was stirred at 70° C. for 1.5 hours, then allowed to cool to r.t.

A solution of (−)-menthyl chloroformate (3.53 mL) in dry THF (15 mL) was added to a solution of 4-methoxypyridine (1.52 mL) in dry THF (35 mL) previously cooled to −78° C. under a nitrogen atmosphere. After 15 minutes, the solution containing the 4-fluoro-2-methyl-phenyl magnesium bromide was added drop-wise, and the mixture was stirred at −78° C. for 1 hour. The reaction was quenched by the addition of 1M hydrochloric acid solution (20 mL), warmed to r.t. and stirred at 23° C. for 30 minutes. After extraction with AcOEt (2×150 mL), the combined organic extracts were washed with brine (50 mL), dried and concentrated in vacuo to a residue, which was purified by flash chromatography (CH/THF/toluene 8:1:1) to give:
1. intermediate 6a (3.44 g—yellow oil)
2. intermediate 6b (530 mg—white solid).

INTERMEDIATE 6a

T.l.c.: CH/THF/toluene 7:2:1, Rf=0.59.
IR (nujol, $cm^{-1}$): 1718 and 1675 (C=O).
NMR ($d_6$-DMSO): δ (ppm) 8.14 (d, 1H); 7.08 (dd, 1H); 7.02 (dd, 1H); 6.95 (m, 1H); 5.68 (d, 1H); 5.34 (d, 1H); 4.47 (m, 1H); 3.26 (dd, 1H); 2.30 (m, 4H); 1.7 (m, 4H); 1.33 (m, 2H); 0.8 (m, 11H).

INTERMEDIATE 6b

M.p.: 117-120° C.
T.l.c.: CH/THF/toluene 7:2:1, Rf=0.56.
IR (nujol, $cm^{-1}$): 1718 and 1669 (C=O).
NMR ($d_6$-DMSO): δ (ppm) 8.17 (d, 1H); 7.04-6.94 (m, 3H); 5.70 (d, 1H); 5.35 (d, 1H); 4.42 (m, 1H); 3.26 (dd, 1H); 2.30 (m, 4H); 1.58-1.40 (m, 3H); 1.2-0.7 (m, 8H); 0.51-0.34 (bs, 6H):

INTERMEDIATE 7

2-(R)-(4-Fluoro-2-Methyl-phenyl)-2,3-dihydro-1H-pyridin-4-one

Sodium methoxide (100 mg) was added to a solution of intermediate 6b (170 mg) in MeOH (15 mL) under a nitrogen atmosphere. The mixture was refluxed for two hours, and the solvent was removed in vacuo. The residue was partitioned between water (10 mL) and AcOEt (15 mL). The layers were separated, and the aqueous phase was extracted with further AcOEt (4×10 mL). The combined organic extracts were washed with brine (10 mL), dried and concentrated in vacuo to give the title compound (145 mg) as a light yellow oil.

NMR ($d_6$-DMSO): δ (ppm) 7.71 (bd, 1H); 7.45 (dd, 1H); 7.38 (t, 1H); 7.03 (m, 2H); 4.86 (dd, 1H); 4.77 (d, 1H); 2.42 (dd, 1H); 2.31 (m, 4H).
MS (ES/+): m/z=206 $[M+H]^+$.

INTERMEDIATE 8

2-(R)-(4-Fluoro-2-methyl-phenyl)-piperidin-4-one

Palladium over charcoal (10%-74 mg) was added to a solution of intermediate 7 (145 mg) in MeOH (8 mL) and THF (2 mL). The mixture was allowed to react with hydrogen in a pressure reactor (2 atm) overnight. After flushing with nitrogen, the solution was filtered and the solvent removed in vacuo. The crude product was purified by flash chromatography (AcOEt/MeOH 9:1) to give the title compound (26 mg) as a yellow oil.

The enantiomeric excess (90-95%) was detected by chiral HPLC.

T.l.c.: AcOEt/MeOH 9:1, Rf=0.2.
NMR ($d_6$-DMSO): δ (ppm) 7.49 (dd, 1H); 7.00 (m, 2H); 3.97 (dd, 1H); 3.27 (m, 1H); 2.82 (dt, 1H); 2.72 (bm, 1H); 2.47 (m, 1H); 2.40 (m, 1H); 2.29 (s, 3H); 2.25 (dt, 1H); 2.18 (m, 1H).
MS (ES/+): m/z=208 $[MH]^+$. $[\alpha]_D$=+82.1 (c=1.07, DMSO).

INTERMEDIATE 9

2-(R)-(4-Fluoro-2-methyl-phenyl)-piperidin-4-one mandelic acid

A solution of L-(+)-mandelic acid (22.6 g) in AcOEt (308 mL) was added to a solution of intermediate 2 (31 g) in AcOEt (308 mL). Then isopropanol (616 mL) was added and the solution was concentrated in vacuo to 274 mL. The solution was then cooled to 0° C. and further cold isopropanol (96 mL) was added. The thick precipitate was stirred under nitrogen for 5 hours at 0° C., then filtered and washed with cold Et2O (250 mL) to give the title compound as a pale yellow solid (20.3 g).

M.p.: 82-85° C.

NMR (d$_6$-DMSO): δ (ppm) 7.51 (dd, 1H); 7.40 (m, 2H); 7.32 (m, 2H); 7.26 (m, 1H); 7.0 (m, 2H); 4.95 (s, 1H); 4.04 (dd, 1H); 3.31 (m, 1H); 2.88 (m, 1H); 2.49-2.2 (m, 4H); 2.29 (s, 3H).

Chiral HPLC: HP 1100 HPLC system; column Chiralcel OD-H, 25 cm×4.6 mm; mobile phase: n-hexane/isopropanol 95:5+1% diethylamine; flow: 1.3 ml/min; detection: 240/215 nm; retention time 12.07 minutes.

INTERMEDIATE 10

2-(R)-4-Fluoro-2-methyl-phenyl)-4-oxo-piperidine-1-carboxylic acid, (3,5-bis-trifluoromethyl-benzyl)-methylamide Method A A solution of triphosgene (17 mg) in dry DCM (2 mL) was added to a solution of intermediate 8 (26 mg) and DIPEA (65 mg) in dry DCM (3 mL) previously cooled to 0° C. under a nitrogen atmosphere. After two hours acetonitrile (10 mL) was added, the temperature was allowed to reach r.t. and the DCM evaporated under a nitrogen flush. Then, a solution of 3,5-(bis-trifluoromethyl-benzyl)-methylamine hydrochloride (74 mg) and DIPEA (130 mg) in acetonitrile (3 mL) was added and the mixture was stirred at 23° C. overnight. The solvent was concentrated in vacuo. The residue was dissolved in AcOEt (10 mL) and washed with 1N hydrochloric acid solution (3×5 mL), 5% sodium hydrogen carbonate (5 mL) and brine (10 mL). The organic layer was dried and concentrated in vacuo to a residue, which was purified by flash chromatography (CH/AcOEt 1:1) to give the title compound (50 mg) as a white solid.

Method B

A saturated sodium hydrogen carbonate solution (348 mL) was added to a solution of intermediate 9 (23.2 g) in AcOEt (348 mL) and the resulting mixture was vigorously stirred for 15 minutes. The aqueous layer was back-extracted with further AcOEt (230 mL) and the combined organic extracts were dried and concentrated in vacuo to give intermediate 8 (12.31 g) as a yellow oil, which was treated with TEA (20.5 mL) and AcOEt (123 mL). The solution obtained was added drop-wise over 40 minutes to a solution of triphosgene (8 g) in AcOEt (61 mL) previously cooled to 0° C. under a nitrogen atmosphere, maintaining the temperature between 0° C. and 8° C. After stirring for 2 hours at 20° C., 3,5-(bis-trifluoromethyl-benzyl)-methylamine hydrochloride (28.1 g), AcOEt (184 mL) and TEA (33 mL) were added to the reaction mixture which was then further stirred for 2 hours at 20° C.

The solution was washed with 10% sodium hydroxide solution (3×185 mL) and 1% hydrochloric acid solution (3×185 mL). The organic layer was dried and concentrated in vacuo to a crude (38 g), which was purified through a silica pad (CH/AcOEt from 9:1 to 1:1) to give the title compound (24.7 g) as a colourless oil.

NMR (d$_6$-DMSO): δ (ppm) 7.96 (s, 1H); 7.76 (s, 2H); 7.26 (dd, 1H); 6.98 (dd, 1H); 6.90 (td, 1H); 5.23 (t, 1H); 4.61 (d, 1H); 4.41 (d, 1H); 3.60 (m, 2H); 2.69 (m, 2H); 2.79 (s, 3H); 2.50 (m, 2H); 2.27 (s, 3H).

MS (ES/+): m/z=491 [MH]$^+$.

INTERMEDIATE 11

4-Cyclopropanoyl-piperazine-1-carboxylic acid, tert-butyl ester

Cyclopropanoyl chloride (112 μL) was added to a mixture of N-tert-butoxycarbonylpiperazine (200 mg) and an excess of potassium carbonate in anhydrous DCM (10 mL) under a nitrogen atmosphere. The mixture was stirred at r.t. for 18 hours, then it was filtered off from inorganics. The organic phase was diluted with Et2O (20 mL) and washed with 1N hydrochloric acid solution (10 mL). The aqueous phase was made basic with 1N sodium hydroxide solution and extracted twice with DCM. The combined organic layers were dried and concentrated in vacuo to give the title compound (210 mg) as an oil.

T.l.c.: AcOEt, Rf=0.45.

NMR (d$_6$-DMSO): δ (ppm) 3.64-3.28 (m, 8H); 1.94 (m, 1H); 1.4 (s, 9H); 0.7 (m, 4H).

MS (ES/+): m/z=255 [M+H]$^+$.

INTERMEDIATE 12

1-Cyclopropanoyl-piperazine

TFA (965 μL) was added to a solution of intermediate 11 (210 mg) in anhydrous DCM (1 mL). The solution was stirred at r.t. for 2 hours, then it was concentrated in vacuo. The residue was diluted in a saturated potassium carbonate solution (10 mL) and extracted with AcOEt (2×20 mL). The combined organic extracts were dried and concentrated in vacuo to give the title compound (110 mg) as an oil.

T.l.c.: AcOEt, Rf=0.14.

IR (CDCl$_3$, cm$^{-1}$): 1626 (C=O).

NMR (CDCl$_3$): δ (ppm) 3.7 (bs, 1H); 3.63 (bd, 4H); 2.88 (bd, 4H); 1.72 (m, 1H); 0.99 (m, 2H); 0.75 (m, 2H).

MS (ES/+): m/z=155 [M+H]$^+$.

INTERMEDIATE 13

4-(2-Methyl-propanoyl)-piperazine-1-carboxylic acid, tert-butyl ester

Isopropanoyl chloride (112 μL) was added to a mixture of N-tert-butoxycarbonylpiperazine (200 mg) and an excess of potassium carbonate in anhydrous DCM (10 mL) under a nitrogen atmosphere. The mixture was stirred at r.t. for 18 hours, then it was filtered off from inorganics. The organic phase was diluted with Et2O (20 mL) and washed with 1N hydrochloric acid solution (10 mL). The aqueous phase was made basic with 1N sodium hydroxide solution and extracted twice with DCM. The combined organic layers were dried and concentrated in vacuo and the residue was purified by flash chromatography (AcOEt 100%) to give the title compound (133 mg) as a white solid.

T.l.c.: AcOEt, Rf=0.58.

IR (nujol, cm$^{-1}$): 1703 and 1630 (C=O).

NMR (d$_6$-DMSO): δ (ppm) 3.45-3.4 (m, 4H); 3.3-3.26 (m, 4H); 2.84 (m, 1H); 1.4 (s, 9H); 0.97 (d, 6H).

MS (ES/+): m/z=257 [M+H]$^+$.

INTERMEDIATE 14

1-(2-Methyl-propanoyl)-piperazine

TFA (900 µL) was added to a solution of intermediate 13 (133 mg) in anhydrous DCM (10 mL). The solution was stirred at r.t. for 3.5 hours, then it was concentrated in vacuo. The residue was diluted in a saturated potassium carbonate solution (10 mL) and extracted with AcOEt (2×20 mL). The combined organic extracts were dried and concentrated in vacuo to give the title compound (50 mg) as an oil.

T.l.c.: AcOEt, Rf=0.12.

IR (CDCl$_3$, cm$^{-1}$): 1624 (C=O).

NMR (CDCl$_3$): δ (ppm) 3.7 (bs, 2H); 3.5 (bs, 2H); 2.86 (m, 4H); 2.78 (m, 1H); 1.13 (d, 6H).

MS (ES/+): m/z=157 [M+H]$^+$.

INTERMEDIATE 15

4-(R)-[1-[(3,5-Bis-trifluoromethyl-benzyl)-methyl-carbamoyl]-2-(R)-(4-fluoro-2-methyl-phenyl)-piperidin-4-yl]-piperazine-1-carboxylic acid, tert-butyl ester (15a) and

4-(S)-[1-[(3,5-Bis-trifluoromethyl-benzyl)-methyl-carbamoyl]-2-(R)-(4-fluoro-2-methyl-phenyl)-piperidin-4-yl]-piperazine-1-carboxylic acid, tert-butyl ester (15b)

A solution of intermediate 10 (400 mg) and N-tert-butoxycarbonyl-piperazine (151.8 mg) in dry 1,2-dichloroethane (10 mL) was stirred at r.t. for 30 minutes under a nitrogen atmosphere. Then, sodium triacetoxyborohydride (310 mg) was added and the mixture was stirred at 23° C. for 24 hours. The solution was diluted with AcOEt and washed with water. The organic layer was dried and concentrated in vacuo to a residue, which was purified by flash chromatography (AcOEt/MeOH from 9:1) to give:
1. intermediate 15a (181 mg),
2. intermediate 15b (155 mg).

INTERMEDIATE 15a

T.l.c.: AcOEt/MeOH 8:2 Rf=0.35.

IR (nujol, cm$^{-1}$): 1703 and 1651 (C=O).

NMR (d$_6$-DMSO): δ (ppm) 7.91 (s, 1H); 7.65 (s, 2H); 7.26 (dd, 1H); 6.89 (dd, 1H); 6.79 (bt, 1H); 4.78 (dd, 1H); 4.52 (d, 1H); 4.37 (d, 1H); 3.25 (m, 6H); 3.09 (m, 1H); 2.78 (s, 3H); 2.37 (bs, 4H); 2.22 (s, 3H); 1.86 (m, 1H); 1.78 (m, 1H); 1.68 (m, 2H); 1.35 (s, 9H).

MS (ES/+): m/z=661 [MH]$^+$.

INTERMEDIATE 15b

T.l.c.: AcOEt/MeOH 8:2 Rf=0.14.

IR (nujol, cm$^{-1}$): 1702 and 1654 (C=O).

NMR (d$_6$-DMSO): δ (ppm) 7.90 (s, 1H); 7.56 (s, 2H); 7.18 (dd, 1H); 6.85 (dd, 1H); 6.73 (dt, 1H); 4.59 (d, 1H); 4.32 (d, 1H); 4.1 (dd, 1H); 3.41 (bm, 1H); 3.21 (bs, 4H); 2.87 (s, 3H); 2.64 (t, 1H); 2.5 (m, 1H); 2.39 (bs, 4H); 2.3 (s, 3H); 1.82 (bs, 1H); 1.73 (m, 1H); 1.56 (dq, 1H); 1.33 (s, 9H); 1.33 (q, 1H).

MS (ES/+): m/z=661 [MH]$^+$.

INTERMEDIATE 16

1-(Benzyloxycarbonyl)-2-(4-fluoro-phenyl)-2,3-dihydro-4-pyridone

A solution of benzyl chloroformate (48.7 mL) in dry THF (60 mL) was added to a solution of 4-methoxypyridine (25 mL) in dry THF (900 mL) previously cooled at −23° C. under a nitrogen atmosphere.

The mixture was stirred at −23° C. for 50 minutes, then p-fluorophenyl magnesium bromide (1M in THF—48.7 mL) was added. The solution was stirred at −20° C. for 1 hour, then it was warmed up to 20° C. and a 10% hydrochloric acid solution (560 mL) was added. The aqueous layer was extracted with AcOEt (1000 mL).

The organic extract was washed with 5% sodium hydrogen carbonate solution (600 mL) and brine (600 mL) then partially concentrated in vacuo. CH (200 mL) was added drop-wise over 1 hour at 20° C. and the resulting mixture was stirred at r.t. for 10 minutes, then at 0° C. for 1.5 hours. The solid obtained was filtered off to give the title compound as a white solid (51.6 g).

NMR (d$_6$-DMSO): δ (ppm) 8.05 (d, 1H); 7.4-7.3 (m, 5H); 7.24 (dd, 2H); 7.15 (t, 1H); 5.73 (d, 1H); 5.29 (d, 1H); 5.24 (dd, 2H); 3.25 (dd, 1H); 2.62 (d, 1H); 2.26 (s, 3H).

MS (EI/+): m/z=325 [M]$^+$.

INTERMEDIATE 17

1-Benzyloxycarbonyl 2-(4-fluoro-phenyl)-piperidine-4-one

L-selectride (1M solution in THF, 62 mL) was added dropwise, over 80 minutes, to a solution of intermediate 16 (20 g) in dry THF (300 mL) previously cooled to −72° C. under a nitrogen atmosphere. After 45 minutes, the solution was allowed to warm to −30° C. and 2% sodium hydrogen carbonate solution (280 mL) was added drop-wise. The solution was extracted with AcOEt (3×280 mL). The combined organic phases were washed with water (80 mL) and brine (160 mL). The organic phase was dried and concentrated in vacuo to give the title compound as a pale yellow oil (27 g).

NMR (d$_6$-DMSO): δ (ppm) 7.26 (m, 7H); 7.17 (t, 2H); 5.53 (bt, 1H); 5.12 (m, 2H); 4.1 (m, 1H); 3.44 (m, 1H); 3.01-2.84 (2dd, 2H); 2.54-2.3 (m, 2H).

INTERMEDIATE 18

2-(4-Fluoro-phenyl)-piperidine-4-one

Intermediate 17 (94 g) was dissolved in AcOEt (300 mL), then 10% Pd/C (6.8 g) was added under a nitrogen atmosphere. The slurry was hydrogenated at 1 atmosphere for 3 hours. The mixture was filtered through Celite and the organic phase was concentrated in vacuo to give the crude 2-(4-fluoro-phenyl)-piperidine-4-one (10 g).

A part of this material (9 g) was purified by flash chromatography (from CH/AcOEt 7:3 to AcOEt 100%) to give the title compound as a yellow oil (5 g).

NMR (d$_6$-DMSO): δ (ppm) 7.43 (m, 2H); 7.15 (m, 2H); 3.86 (dd, 1H); 3.29 (m, 1H); 2.87 (bs, 1H); 2.81 (m, 1H); 2.48 (m, 1H); 2.42 (m, 1H); 2.33 (m, 1H); 2.19 (m, 1H).

INTERMEDIATE 19

2-(4-Fluoro-phenyl)-piperidine-4-one, L-(+)-mandelate

L-(+)-mandelic acid (2.6 g) was added to a solution of intermediate 18 (3.3 g) in acetone (50 mL) at r.t. The mixture was stirred at r.t. for 3 hours and at 0° C. for 30 minutes, then the solid was filtered off to give the title compound as a white solid (4.4 g).

M.p.: 123-124° C.

NMR ($d_6$-DMSO): δ (ppm) 7.39 (m, 2H); 7.35 (d, 2H); 7.27 (t, 2H); 7.2 (t, 1H); 7.11 (t, 2H); 4.86 (s, 1H); 3.83 (dd, 1H); 3.3-2.78 (m, 2H); 2.6-2.35 (m, 2H); 2.3-2.15 (m, 2H).

INTERMEDIATES 20a AND 20b 2-(R)-(4-Fluoro-phenyl)-4-oxo-piperidine-1-carboxylic acid, [1-(R)-3,5-bis-trifluoromethyl-phenyl)-ethyl]-methylamide (20a) and 2-(S)-(4-Fluoro-phenyl)-4-oxo-piperidine-1-carboxylic acid, [1-(R)-3,5-bis-trifluoromethyl-phenyl)-ethyl]-methylamide (20b)

Intermediate 19 (600 mg) was treated with a saturated potassium carbonate solution (60 mL) and extracted with AcOEt (3×30 mL). The combined organic extracts were dried and concentrated in vacuo to give 2-(4-fluoro-phenyl)-piperidine-4-one (267 mg). A solution of triphosgene (205 mg) dissolved in dry DCM (2 mL) was added drop-wise to a solution of 2-(4-fluoro-phenyl)-piperidine-4-one (267 mg) and TEA (800 μL) in dry DCM (9 mL) previously cooled to 0° C. under a nitrogen atmosphere. The mixture was stirred at 0° C. for 3 hours and during this time further TEA (800 μL) and triphosgene (205 mg) were added until complete disappearance of the starting material. Then, [1-(R)-3,5-bis-trifluoromethyl-phenyl)-ethyl]-methylamine hydrochloride (560 mg) and DIPEA (1 mL) in dry acetonitrile (15 mL) were added and the mixture was heated to 70° C. for 16 hours. The mixture was allowed to cool to r.t., taken up with AcOEt (30 mL), washed with a cold 1N hydrochloric acid solution (3×15 mL) and brine (3×20 mL). The organic layer was dried and concentrated in vacuo to a residue, which was purified by flash chromatography (CH/AcOEt 7:3) to give:

3. intermediate 20a (140 mg) as a yellow oil,
4. intermediate 20b (195 mg) as a yellow oil.

INTERMEDIATE 20a

T.l.c.: CH/AcOEt 1:1, Rf=0.65.

IR (film, cm$^{-1}$): 1719 and 1636 (C=O).

NMR ($d_6$-DMSO): δ (ppm) 8.0 (s, 1H); 7.87 (s, 2H); 7.3 (dd, 2H); 7.11 (t, 2H); 5.19 (m, 2H); 3.68 (m, 1H); 3.36 (m, 1H); 2.8 (m, 2H); 2.66 (s, 3H); 2.58 (m, 2H); 2.3 (m, 1H); 1.59 (d, 3H).

MS (ES/+): m/z=491 [M+H]$^+$.

INTERMEDIATE 20b

T.l.c.: CH/AcOEt 1:1, Rf=0.49.

IR (film, cm$^{-1}$): 1721 and 1639 (C=O).

NMR ($d_6$-DMSO): δ (ppm) 7.97 (s, 1H); 7.82 (s, 2H); 7.29 (dd, 2H); 7.1 (dd, 1H); 5.21 (q, 1H); 5.11 (t, 1H); 3.6 (m, 1H); 3.46 (m, 1H); 2.85-2.7 (2dd, 2H); 2.76 (s, 3H); 2.56 (m, 1H); 2.39 (m, 1H); 1.54 (d, 3H).

MS (ES/+): m/z=491 [M+H]$^+$.

EXAMPLE 1

4-(R)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide (1a)

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide (1b)

A solution of intermediate 4a (120 mg), 1-acetylpiperazine (29.8 mg) and sodium triacetoxyborohydride (126 mg) in dry 1,2-dichloroethane (5 mL) was stirred at 23° C. for 24 hours under a nitrogen atmosphere. The solution was washed with a 5% sodium hydrogen carbonate solution (15 mL) and brine (10 mL). The organic layer was dried and concentrated in vacuo to a residue which was purified by flash chromatography (AcOEt/MeOH 7:3) to give:

1. 4-(R)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide (40.0 mg—T.l.c.: AcOEt/MeOH 6:4 Rf=0.37),
2. 4-(S)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide (30.0 mg—T.l.c.: AcOEt/MeOH 6:4 Rf=0.36).

EXAMPLE 2

4-(R)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide hydrochloride A solution of example 1a (40.0 mg) in dry Et2O (5 mL) was treated with hydrochloric acid (1M in Et2O—1 mL). The resulting solution was stirred at 23° C. for 30 minutes, then it was concentrated in vacuo to give the title compound as a white solid (41.2 mg).

IR (nujol, cm$^{-1}$): 3416 (NH$^+$), 1652 (C=O).

NMR ($d_6$-DMSO): δ (ppm) 10.35 (bs, 1H); 8.00 (s, 1H); 7.77 (s, 2H); 7.37 (dd, 1H); 7.01 (dd, 1H); 6.93 (dt, 1H); 5.25 (bm, 1H); 5.06 (q, 1H); 4.44 (bm, 1H); 3.99 (m, 1H); 3.70-3.45 (m, 4H); 3.20-2.90 (2m, 4H); 2.15 (m, 2H); 1.90-1.75 (2m, 3H); 2.04 (s, 3H); 1.57 (d, 3H).

MS (ES/+): m/z=617 [MH-HCl]$^+$.

EXAMPLE 3

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide hydrochloride A solution of example 1b (30.0 mg) in dry Et2O (5 mL) was treated with hydrochloric acid (1M in Et2O—1 mL). The resulting mixture was stirred at 23° C. for 15 minutes, then filtered; the filtrate was treated with further dry Et2O (2 mL) to give the title compound as a whitish solid (26.5 mg).

IR (nujol, cm$^{-1}$): 3383 (NH$^+$), 1650 (C=O).

NMR (d$_6$-DMSO): δ (ppm) 11.17 (bs, 1H); 7.98 (s, 1H); 7.67 (s, 2H); 7.21 (t, 1H); 6.94 (dd, 1H); 6.82 (dt, 1H); 5.3 (q, 1H); 4.4 (bd, 1H); 4.18 (dd, 1H); 3.96-3.42 (m, 5H); 3.10-2.70 (m, 4H); 2.72 (s, 3H); 2.43 (s, 3H); 2.17 (m, 2H); 2.00 (s, 3H); 1.73-1.24 (m, 3H); 1.45 (d, 3H).

MS (ES/+): m/z=617 [MH-HCl]$^+$.

EXAMPLE 4

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide methanesulphonate A solution of intermediate 4a (7.7 g) in acetonitrile (177 mL) was added to a solution of 1-acetyl-piperazine (3.9 g) in acetonitrile (17.7 mL) followed by sodium triacetoxyborohydride (6.4 g) under a nitrogen atmosphere.

The reaction mixture was stirred at room temperature for 24 hours and then quenched with a saturated sodium hydrogen carbonate (23.1 mL) and water (61.6 mL). The resulting solution was concentrated in vacuo, then AcOEt (208 mL) was added; the layers were separated and the aqueous layer was back-extracted with further AcOEt (2×77 mL). The collected organic phases were washed with brine (2×118 mL), dried and concentrated in vacuo to give the crude mixture of syn and anti diastereomers (nearly 1:1) as a white foam (9.5 g).

A solution of this intermediate in THF (85.4 mL) was added to a solution of methansulfonic acid (0.890 mL) in THF (6.1 mL) at r.t. After seeding, the desired syn diastereomer started to precipitate. The resulting suspension was stirred for 3 hours at 0° C. and then filtered under a nitrogen atmosphere. The resulting cake was washed with cold THF (15.4 mL) and dried in vacuo at +20° C. for 48 hours to give the title compound as a white solid (4.44 g).

NMR (d$_6$-DMSO): δ (ppm) 9.52 (bs, 1H); 7.99 (bs, 1H); 7.68 (bs, 2H); 7.23 (m, 1H); 6.95 (dd, 1H); 6.82 (m, 1H); 5.31 (q, 1H); 4.45 (bd, 1H); 4.20 (dd, 1H); 3.99 (bd, 1H); 3.65-3.25 (bm, 5H); 3.17 (m, 1H); 2.96 (m, 1H); 2.88-2.79 (m+m, 2H); 2.73 (s, 3H); 2.36 (s, 3H); 2.30 (s, 3H); 2.13-2.09 (bd+bd, 2H); 2.01 (s, 3H); 1.89-1.73 (m+m, 2H); 1.46 (d, 3H).

m.p 243.0° C.

The compound is isolated in a crystalline form.

EXAMPLE 5

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide sulfate Sulfuric acid 96% was added (0.06 mL) to a solution of example 1b (0.65 g) in THF (6.5 mL) at 23° C. under a nitrogen atmosphere. The suspension was stirred at 23° C. for 15 hours, then cooled to 4° C., stirred for 4 hours and allowed to warm to r.t. The solid was filtered off and dried at 23° C. for 18 hours to give the title compound (0.681 g).

NMR (d$_6$-DMSO): δ (ppm) 9.58 (bs, 1H); 7.99 (bs, 1H); 7.68 (bs, 2H); 7.23 (m, 1H); 6.95 (dd, 1H); 6.83 (m, 1H); 5.31 (q, 1H); 4.45 (bd, 1H); 4.20 (d, 1H); 3.98 (bm, 1H); 3.65-3.30 (bm, 5H); 3.20-2.70 (bm, 4H); 2.74 (s, 3H); 2.36 (s, 3H); 2.13 (bd, 1H); 2.08 (bd, 1H); 2.02 (s, 3H); 1.87 (m, 1H); 1.72 (m, 1H); 1.46 (d, 3H).

m.p. 237.4

The compound is isolated in a crystalline form.

EXAMPLE 6

4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methyl-amide p-toluenesulfonate Para-toluenesulfonic acid monohydrate (0.20 g) was added to a solution of example 1b (0.65 g) in THF (6.5 mL) at 23° C. under a nitrogen atmosphere. Isooctane (10 mL) was added and the suspension was stirred at 23° C. for 24 hours. The solid was filtered off and dried at 23° C. for 18 hours to give the title compound (0.567 g).

NMR (d$_6$-DMSO): δ (ppm) 9.53 (bs, 1H); 8.00 (bs, 1H); 7.68 (bs, 2H); 7.46 (d, 2H); 7.22 (bm, 1H); 7.10 (d, 2H); 6.95 (dd, 1H); 6.82 (m, 1H); 5.30 (q, 1H); 4.45 (bd, 1H); 4.19 (d, 1H); 3.99 (bm, 5H); 3.65-3.05 (m, 3H); 3.05-2.70 (m, 2H); 2.73 (s, 3H); 2.35 (s, 3H); 2.27 (s, 3H); 2.12 (m, 1H); 2.07 (m, 1H); 2.02 (s, 3H) 1.87 (m, 1H); 1.72 (m, 1H); 1.46 (d, 3H).

EXAMPLES 7

4-(R)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide hydrochloride (7a)

4-(S)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide hydrochloride (7b)

A solution of intermediate 10 (86.7 mg), 1-acetylpiperazine (22 mg) and sodium triacetoxyborohydride (67 mg) in dry 1,2-dichloroethane (5 mL) was stirred at 23° C. for 24 hours under a nitrogen atmosphere. The solution was washed with a 5% sodium hydrogen carbonate solution (15 mL) and brine (10 mL). The organic layer was dried and concentrated in vacuo to a residue which was purified by flash chromatography (AcOEt/MeOH 7:3) to give:

1. 4-(R)-(4-acetyl-piperazin-1-yl)-2-(R)-(4-fluoro-2-methyl-phenyl)-piperidine-1-carboxylic acid, (3,5-bis-trifluoromethyl-benzyl)-methylamide (34.6 mg hereinafter compound 1);
2. 4-(S)-(4-acetyl-piperazin-1-yl)-2-(R)-(4-fluoro-2-methyl-phenyl)-piperidine-1-carboxylic acid, (3,5-bis-trifluoromethyl-benzyl)-methylamide (19 mg hereinafter compound 2).

EXAMPLE 7A

A solution of compound 1 (33 mg) in dry Et2O (2 mL) was treated with hydrochloric acid (1M in Et2O—0.5 mL). The resulting solution was stirred at 23° C. for 30 minutes. The solution was concentrated in vacuo to give the title compound as a white foam (30 mg).

IR (nujol, cm$^{-1}$): 3395 (NH$^+$), 1632 (C=O).

NMR (d$_6$-DMSO): δ (ppm) 10.35 (bs, 1H); 7.98 (bs, 1H); 7.8 (bs, 2H); 7.37 (dd, 1H); 7.0 (dd, 1H); 6.92 (m, 1H); 5.24 (m, 1H); 4.57 (d, 1H); 4.41 (d, 1H); 4.45 (bm, 1H); 3.99 (bm, 1H); 3.8-3.4 (bm, 6H); 3.2-2.8 (m, 4H); 2.73 (s, 3H); 2.34 (2H); 2.23 (s, 3H); 2.03 (s, 3H); 2.17 (1H); 1.69 (m, 1H).

MS (ES/+): m/z=603 [MH–HCl]$^+$.

EXAMPLE 7B

A solution of compound 2 (19 mg) in dry Et2O (5 mL) was treated with hydrochloric acid (1M in Et2O—1 mL). The resulting mixture was stirred at 23° C. for 15 minutes, then concentrated in vacuo to give the title compound as a white foam (14 mg).

IR (nujol, cm$^{-1}$): 3387 (NH$^+$), 1652 (C=O).

NMR (d$_6$-DMSO): δ (ppm) 11.77 (bs, 1H); 7.94 (s, 1H); 7.58 (s, 2H); 7.24 (t, 1H); 6.93 (dd, 1H); 6.81 (m, 1H); 4.62 (d, 1H); 4.4 (dd, 1H); 4.35 (d, 1H); 4.19 (dd, 1H); 3.8-3.4 (m, 4H); 3.2-2.7 (m, 4H); 3.9-1.25 (m, 6H); 2.92 (s, 3H); 2.35 (s, 3H); 2.00 (s, 3H).

MS (ES/+): m/z=603 [MH–HCl]$^+$, 625 [M–HCl+Na]$^+$.

EXAMPLE 8

2-(R)-(4-Fluoro-2-methyl-phenyl)-4-(R,S)-(4-methyl-piperazin-1-yl)-piperidine-1-carboxylic acid, [1-(R)-(3,5-bis-trifluoromethyl-phenyl)-ethyl]-methylamide hydrochloride A solution of intermediate 4a (100 mg), N-methylpiperazine (22 μL) and sodium triacetoxyborohydride (64 mg) in dry 1,2-dichloroethane (5 mL) was stirred at 23° C. for 6 hours under a nitrogen atmosphere. The solution was washed with a 5% sodium hydrogen carbonate solution (10 mL) and brine (10 mL). The organic layer was dried and concentrated in vacuo to a residue, which was purified by flash chromatography (AcOEt/MeOH from 95:5 to 8:2) to give 2-(R)-(4-fluoro-2-methyl-phenyl)-4-(R,S)-(4-methyl-1-piperazinyl)-piperidine-1-carboxylic acid, [1-(R)-(3,5-bis-trifluoromethyl-phenyl)-ethyl]-methylamide (57 mg T.l.c.: AcOEt/MeOH 8:2, Rf=0.2) which was dissolved in dry Et2O (5 mL) and then treated with hydrochloric acid (1M in Et2O—2 mL) and the resulting solution was stirred at 23° C. for 5 minutes. The solution was concentrated in vacuo to give a solid which was triturated in Et2O (2 mL) to give the title compound as a white solid (35.4 mg).

IR (nujol, cm$^{-1}$): 3405 (NH$_2^+$), 1639 (C=O).

NMR (d$_6$-DMSO): δ (ppm) 7.95 (s, 2H); 7.71 (s, 2H); 7.67 (s, 2H); 7.26 (dd, 1H); 7.15 (dd, 1H); 6.93 (dd, 1H); 6.87 (dd, 1H); 6.82 (m, 1H); 6.74 (m, 1H); 5.32 (q, 1H); 5.16 (q, 1H); 4.84 (m, 1H); 4.12 (dd, 1H); 3.5-3.0 (m, 3H); 2.69 (s, 3H); 2.61 (s, 3H); 2.32 (s, 3H); 2.24 (s, 3H); 2.13 (s, 3H); 2.09 (s, 3H); 2.5-1.5 (m, 12H); 1.50 (d, 3H); 1.45 (d, 3H).

MS (ES/+): m/z=589 [MH–HCl]$^+$.

EXAMPLE 9

2-(R)-(4-Fluoro-2-methyl-phenyl)-4-(S)-piperazin-1-yl-piperidine-1-carboxylic acid, [1-(R)-(3,5-trifluoromethyl-phenyl)-ethyl]-methylamide hydrochloride A solution of intermediate 4a (160 mg), N-tert-butoxycarbonyl-piperazine (60 mg) and sodium triacetoxyborohydride (100 mg) in dry 1,2-dichloroethane (12 mL) was stirred at 23° C. for 24 hours under a nitrogen atmosphere. The solution was washed with a 5% sodium hydrogen carbonate solution (20 mL) and brine (20 mL). The organic layer was dried and concentrated in vacuo to a residue, which was purified by flash chromatography (CH/AcOEt from 1:1 to 3:7) to give:

1. 2-(R)-(4-Fluoro-2-methyl-phenyl)-4-(R)-[(4-tert-butoxycarbonyl)-piperazin-1-yl]-piperidine-1-carboxylic acid, [1-(R)-(3,5-bis-trifluoromethyl-phenyl)-ethyl]-methylamide (74 mg—T.I.c.: CH/AcOEt 1:1, Rf=0.35 hereinafter compound 1)
2. -2-(R)-(4-Fluoro-2-methyl-phenyl)-4-(S)-[(4-tert-butoxycarbonyl)-piperazin-1-yl]-piperidine-1-carboxylic acid, [1-(R)-(3,5-bis-trifluoromethyl-phenyl)-ethyl]-methylamide (48 mg—T.I.c.: CH/AcOEt 1:1, Rf=0.19 hereinafter compound 2)

Trifluoroacetic acid (1 mL) was added drop-wise at 0° C. to a solution of compound 2 (48 mg) in dry DCM (3 mL). The solution was stirred for 1 hour at the same temperature and for 1 hour at r.t. Then the solvent was removed in vacuo and the crude dissolved in AcOEt (5 mL). The resulting solution was washed with a saturated potassium carbonate solution and dried. After concentration in vacuo, the crude 2-(R)-(4-fluoro-2-methyl-phenyl)-4-(S)-piperazin-1-yl-piperidine-1-carboxylic acid [1-(R)-(3,5-bis-trifluoromethyl-phenyl)-ethyl]-methylamide (18 mg) was dissolved in dry Et2O (1 mL) and was then treated with hydrochloric acid (1M in Et2O—220 μL) at 0° C. The resulting mixture was stirred at r.t. for 30 minutes, then filtered and triturated with n-pentane to give the title compound as a whitish solid (15 mg).

IR (nujol, cm$^{-1}$): 1653 (C=O).

NMR (d$_6$-DMSO): δ (ppm) 7.94 (s, 1H); 7.59 (s, 2H); 7.22 (dd, 1H); 6.89 (dd, 1H); 6.77 (m, 1H); 4.62 (d, 1H); 4.36 (d, 1H); 4.13 (dd, 1H); 3.44 (m, 1H); 3.3 (m, 1H); 2.9 (s, 3H); 2.67 (m, 1H); 2.65 (m, 4H); 2.4 (bm, 4H); 2.34 (s, 3H); 1.86 (bd, 1H); 1.77 (bd, 1H); 1.6 (dq, 1H); 1.34 (q, 1H).

MS (ES/+): m/z=561 [MH–HCl]$^+$.

EXAMPLE 10

2-(R)-(4-Fluoro-2-methyl-phenyl)-4-(R,S)-(4-methyl-piperazin-1-yl)-piperidine-1-carboxylic acid, (3,5-bis-trifluoromethyl-benzyl)-methylamide dihydrochloride A solution of intermediate 10 (120 mg) and N-methylpiperazine (41 μL) in dry 1,2-dichloroethane (2 mL) and acetonitrile (2 mL) was stirred at r.t. for 1 hour under a nitrogen atmosphere. Then sodium triacetoxyborohydride (78 mg) was added and the mixture was stirred at 23° C. for 18 hours. The solution was washed with a 5% sodium hydrogen carbonate solution (10 mL) and extracted with DCM (2×10 mL). The combined organic extracts were washed with brine (10 mL), dried and concentrated in vacuo to a residue, which was purified by flash chromatography (AcOEt/MeOH 1:1) to give 2-(R)-(4-fluoro-2-methyl-phenyl)-4-(R,S)-(4-methyl-piperazin-1-yl)-piperidine-1-carboxylic acid, (3,5-bis-trifluoromethyl)-benzyl-methylamide (115 mg T.I.c.: AcOEt/MeOH 1:1, Rf=0.09), which was dissolved in dry Et2O (5 mL) then treated with hydrochloric acid (1M in Et2O—0.5 mL) and the resulting mixture was stirred at 23° C. for 5 minutes. The mixture was concentrated in vacuo to a solid which was triturated in Et2O (2 mL) to give the title compound as a whitish solid (115 mg).

M.p.: 208-9° C.

IR (nujol, cm$^{-1}$): 3384 (NH$^+$), 1645 (C=O).

NMR (d$_6$-DMSO): δ (ppm) 7.9 (s, 1H); 7.7 (s, 1H); 7.59 (s, 1H); 7.4 (s, 1H); 7.24 (t, 1H); 6.95-6.82 (m, 2H); 4.63 (d, 1H); 4.59 (d, 1H); 4.36 (d, 1H); 4.21 (d, 1H); 4.19 (d, 1H); 2.93 (s, 3H); 2.37 (s, 3H); 2.27 (s, 3H); 3.7-1.0 (m, 17H).

MS (ES/+): m/z=575 [M+H−2HCl]$^+$.

EXAMPLE 11

4-(R)-(4-Cyclopropanoyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide (11a)

4-(S)-(4-Cyclopropanoyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide (11b)

A solution of intermediate 4a (100 mg) and intermediate 12 (31 mg) in dry 1,2-dichloroethane (5 mL) and acetonitrile (1 mL) was stirred at r.t. for 30 minutes under a nitrogen atmosphere. Then, sodium triacetoxyborohydride (42 mg) was added and the mixture was stirred at 23° C. for 24 hours. The solution was diluted with AcOEt and washed with water. The organic layer was dried and concentrated in vacuo to a residue which was purified by flash chromatography (AcOEt/MeOH 9:1) to give:
example 11A (2 mg—T.I.c.: AcOEt/MeOH 8:2 Rf=0.33),
example 11B (7 mg—T.I.c.: AcOEt/MeOH 8:2 Rf=0.16).

EXAMPLE 12

4-(S)-(4-Cyclopropanoyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide hydrochloride A solution of example 11b (7 mg) in dry Et2O (5 mL) was treated with hydrochloric acid (1M in Et2O—40 µL). The resulting mixture was stirred at 23° C. for 15 minutes, then concentrated in vacuo to give the title compound as a whitish solid (7.2 mg).

IR (nujol, cm$^{-1}$): 3395 (NH$^+$), 1644 (C=O).

NMR (d$_6$-DMSO): δ (ppm) 10.13 (bs, 1H); 8.0 (bs, 1H); 7.69 (s, 2H); 7.23 (m, 1H); 6.96 (m, 1H); 6.84 (m, 1H); 5.31 (bq, 1H); 4.44 (bm, 2H); 4.2 (bd, 1H); 3.7-2.9 (bm, 5H); 2.8 (t, 4H); 2.75 (s, 3H); 2.37 (s, 3H); 2.16 (m, 2H); 1.99 (m, 1H); 2.0-1.5 (m, 2H); 1.47 (d, 3H); 0.87 (m, 2H); 0.74 (m, 2H).

MS (ES/+): m/z=643 [MH-HCl]$^+$.

EXAMPLE 13

4-(R)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide (13a)

4-(S)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide (13b)

A solution of intermediate 4a (100 mg) and intermediate 14 (30 mg) in dry 1,2-dichloroethane (5 mL) was stirred at r.t. for 30 minutes under a nitrogen atmosphere. Then, sodium triacetoxyborohydride (42 mg) was added and the mixture was stirred at 23° C. for 24 hours. The solution was diluted with AcOEt and washed with water. The organic layer was dried and concentrated in vacuo to a residue which was purified by flash chromatography (AcOEt/MeOH from 9:1 to 8:2) to give:
example 13a (15 mg—T.I.c.: AcOEt/MeOH 8:2 Rf=0.33),
example 13b (27.5 mg—T.I.c.: AcOEt/MeOH 8:2 Rf=0.25).

EXAMPLE 14

4-(S)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide hydrochloride A solution of example 13b (27.5 mg) in dry Et2O (1 mL) was treated with hydrochloric acid (1M in Et2O—60 µL). The resulting mixture was stirred at 23° C. for 15 minutes, then concentrated in vacuo. The residue was triturated with pentane to give the title compound as a whitish solid (25.8 mg).

IR (nujol, cm$^{-1}$): 3395 (NH$^+$), 1641 (C=O).

NMR (d$_6$-DMSO): δ (ppm) 10.37 (bs, 1H); 8.0 (s, 1H); 7.68 (s, 2H); 7.22 (dd, 1H); 6.94 (dd, 1H); 6.83 (bt, 1H); 5.31 (bq, 1H); 4.46 (bm, 1H); 4.18 (bd, 1H); 4.12 (m, 1H); 3.6-3.4 (m, 5H); 3.1-2.7 (m, 5H); 2.73 (s, 3H); 2.36 (s, 3H); 2.18-2.11 (m, 2H); 1.89 (bq, 1H); 1.73 (q, 1H); 1.46 (d, 3H); 0.98 (bs, 6H).

EXAMPLE 15

4-(S)-[1-[(3,5-Bis-trifluoromethyl-benzyl)-methyl-carbamoyl]-2-(R)-(4-fluoro-2-methyl-phenyl)-piperidin-4-yl]-piperazine-1-carboxylic acid, dimethylamide hydrochloride TEA (74.6 µL) and triphosgene (13.2 mg) were added to a solution of example 17 (50 mg) in anhydrous DCM (2 mL) under a nitrogen atmosphere. The solution was stirred at 23° C. for 2 hours, then DIPEA (31.9 µL) and dimethylamine (2M solution in THF—49 µL) were added. The mixture was stirred at 23° C. for 18 hours, then poured into 1M hydrochloric acid solution (10 mL) and extracted with AcOEt (2×20 mL). The combined organic extracts were dried and concentrated in vacuo to give 4-(S)-[1-[(3,5-bis-trifluoromethyl-benzyl)-methyl-carbamoyl]-2-(R)-(4-fluoro-2-methyl-phenyl)-piperidin-4-yl]-piperazine-1-carboxylic acid, dimethylamide (60 mg).

A solution of this compound (60 mg) in dry Et2O (1 mL) was treated with hydrochloric acid (1M in Et2O—100 µL). The resulting mixture was stirred at 23° C. for 15 minutes, then concentrated in vacuo. The residue was triturated with petroleum to give the title compound as a whitish solid (52 mg).

IR (nujol, cm$^{-1}$): 3382 (NH$^+$), 1652 (C=O).

NMR (d$_6$-DMSO): δ (ppm) 10.34 (bs, 1H); 7.95 (s, 1H); 7.59 (s, 2H); 7.26 (m, 1H); 6.94 (dd, 1H); 6.84 (m, 1H); 4.63 (d, 1H); 4.36 (d, 1H); 4.2 (dd, 1H); 3.6-3.4 (m, 5H); 3.4-3.1 (m, 5H); 2.93 (s, 3H); 2.75 (s, 6H); 2.7 (m, 1H); 2.36 (s, 3H); 2.17 (m, 2H); 1.9-1.65 (m, 2H).

MS (ES/+): m/z=632 [MH-HCl]$^+$.

EXAMPLE 16

4-(S)-[1-[(3,5-Bis-trifluoromethyl-benzyl)-methyl-carbamoyl]-2-(R)-(4-fluoro-2-methyl-phenyl)-piperidin-4-yl]-1-carboxylic acid, methylamide hydrochloride TEA (74.6 µL) and triphosgene (13.2 mg) were added to a solution of example 17 (50 mg) in anhydrous DCM (2 mL) under a nitrogen atmosphere. The solution was stirred at 23° C. for 2 hours, then DIPEA (31.9 µL) and methylamine (2M solution in THF—49 µL) were added. The mixture was stirred at 23° C. for 18 hour, then poured into 1M hydrochloric acid solution (10 mL) and extracted with AcOEt (2×20 mL). The combined organic extracts were dried and concentrated in vacuo to give 4-(S)-[1-[(3,5-bis-trifluoromethyl-benzyl)-methyl-carbamoyl]-2-(R)-(4-fluoro-2-methyl-phenyl)-piperidin-4-yl]-1-carboxylic acid, methylamide (65.3 mg).

A solution of this compound (60 mg) in dry Et2O (1 mL) was treated with hydrochloric acid (1M in Et2O—100 µL). The resulting mixture was stirred at 23° C. for 15 minutes, then concentrated in vacuo. The residue was triturated with petroleum to give the title compound as a whitish solid (55 mg).

IR (nujol, cm$^{-1}$): 3351 (NH$^+$), 1652 (C=O).

NMR (d$_6$-DMSO): δ (ppm) 10.35 (bs, 1H); 7.95 (s, 1H); 7.59 (s, 2H); 7.25 (m, 1H); 6.94 (dd, 1H); 6.84 (m, 1H); 6.68 (bs, 1H); 4.63 (d, 1H); 4.36 (d, 1H); 4.18 (dd, 1H); 4.0 (m, 1H); 3.6-3.4 (m, 5H); 3.1-2.9 (m, 4H); 2.93 (s, 3H); 2.73 (m, 1H); 2.56 (s, 3H); 2.36 (s, 3H); 2.19 (m, 2H); 1.9 (m, 1H); 1.7 (m, 1H).

MS (ES/+): m/z=618 [MH-HCl]$^+$.

EXAMPLE 17

4-(S)-[1-[(3,5-Bis-trifluoromethyl-benzyl)-methyl-carbamoyl]-2-(R)-(4-fluoro-2-methyl-phenyl)-piperidin-4-yl]-piperazine TFA (1 mL) was added to a solution of intermediate 15b (155 mg) in anhydrous DCM (5 mL). The solution was stirred at r.t. for 3 hours, then it was concentrated in vacuo. The residue was diluted in a saturated potassium carbonate solution (10 mL) and extracted with DCM (2×20 mL) and AcOEt (20 mL). The combined organic extracts were dried and concentrated in vacuo to give the title compound (104 mg) as an oil.

T.l.c.: AcOEt/MeOH 8:2 Rf=0.12.

IR (nujol, cm$^{-1}$): 1653 (C=O).

NMR (d$_6$-DMSO): δ (ppm) 7.94 (s, 1H); 7.59 (s, 2H); 7.22 (dd, 1H); 6.89 (dd, 1H); 6.77 (dt, 1H); 4.62 (d, 1H); 4.36 (d, 1H); 4.13 (dd, 1H); 3.44 (dt, 1H); 3.3 (m, 1H); 2.9 (s, 3H); 2.67 (m, 1H); 2.65 (m, 4H); 2.4 (bm, 4H); 2.34 (s, 3H); 1.86 (bd, 1H); 1.77 (bd, 1H); 1.6 (dq, 1H); 1.34 (q, 1H).

MS (ES/+): m/z=561 [MH]$^+$.

EXAMPLE 18

4-(R)-(4-Acetyl-piperazin-1-yl)-2-(R)-(4-fluoro-phenyl)-piperidine-1-carboxylic acid, [1-(R)-(3,5-bis-trifluoromethyl-phenyl)-ethyl]-methylamide (18a)

4-(S)-(4-acetyl-piperazin-1-yl)-2-(R)-(4-fluoro-phenyl)-piperidine-1-carboxylic acid, [1-(R)-(3,6-bis-trifluoromethyl-phenyl)-ethyl]-methylamide (18b)

A solution of intermediate 20a (140 mg), 1-acetylpiperazine (73 mg) and sodium triacetoxyborohydride (121 mg) in dry acetonitrile (8 mL) was stirred at 23° C. for 24 hours under a nitrogen atmosphere. Then, further sodium triacetoxyborohydride (60 mg) was added and the solution was stirred for a further 1 hour. The solution was diluted with AcOEt (20 mL) and washed with a saturated sodium hydrogen carbonate solution (15 mL) and brine (10 mL). The organic layer was dried and concentrated in vacuo to a residue, which was purified by flash chromatography (AcOEt/MeOH from 9:1 to 8:2) to give:

—compound 18a (4 mg) T.I.c.: AcOEt/MeOH 8:2 Rf=0.48);

—compound 18b (20 mg) T.I.c.: AcOEt/MeOH 8:2 Rf=0.40).

EXAMPLE 19

4-(S)-(4-Acetyl-piperazin-1-yl)-2-(R)-(4-fluoro-phenyl)-piperidine-1-carboxylic acid, [1-(R)-(3,5-bis-trifluoromethyl-phenyl)-ethyl]-methylamide hydrochloride A solution of 18b (20 mg) in dry Et2O (1 mL) was treated at −8° C. with hydrochloric acid (1M in Et2O—0.5 mL). The resulting mixture was stirred at 0° C. for 10 minutes, then filtered; the filtrate was triturated with dry pentane (2×2 mL) to give the title compound as a whitish solid (14.7 mg).

NMR (d$_6$-DMSO): δ (ppm) 10.15 (bs, 1H); 7.91 (s, 1H); 7.68 (s, 2H); 7.26 (m, 2H); 7.01 (m, 2H); 5.28 (q, 1H); 4.4 (bd, 1H); 4.09 (dd, 1H); 3.8-3.4 (m, 5H); 3.8-2.8 (m, 4H); 3.1-2.7 (m, 4H); 2.01 (s, 3H); 2.2-1.8 (m, 4H); 1.47 (d, 3H).

MS (ES/+): m/z=603 [MH-HCl]$^+$.

PHARMACY EXAMPLES

A. Capsules/Tablets

| | |
|---|---|
| Active ingredient | 20.0 mg |
| Starch 1500 | 2.5 mg |
| Microcrystalline Cellulose | 200.0 mg |
| Croscarmellose Sodium | 6.0 mg |
| Magnesium Stearate | 1.5 mg |

The active ingredient is blended with the other excipients. The blend can be used to fill gelatin capsules or compressed to form tablets using appropriate punches. The tablets can be coated using conventional techniques and coatings.

B. Tablets

| | |
|---|---|
| Active ingredient | 20.0 mg |
| Lactose | 200.0 mg |
| Microcrystalline Cellulose | 70.0 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

c) Bolus

| Active ingredient | 2-60 mg/ml |
|---|---|
| Sodium phosphate | 1.0-50.0 mg/ml |
| water for injection | qs to 1 ml |

The formulation may be packed in glass ampoules or vials and syringes with a rubber stopper and a plastic/metal overseal (vials only).

D) Infusion

| Active ingredient | 2-60 mg/ml |
|---|---|
| Infusion solution (NaCl 0.9% or 5% dextrose) | qs to 100 ml |

The formulation may be packed in glass vials or plastic bag.

The affinity of the compound of the invention for NK1 receptor was determined using the $NK_1$-receptor binding affinity method measuring in vitro by the compounds' ability to displace [3H]-substance P (SP) from recombinant human $NK_1$ receptors expressed in Chinese Hamster Ovary (CHO) cell membranes. The affinity values are expressed as negative logarithm of the inhibition constant (Ki) of displacer ligands (pKi).

The pKi values obtained as the average of at least two determinations with representative compounds of the invention are given in the following table:

| Example No | pki |
|---|---|
| 2 | 9.36 |
| 3 | 10.29 |
| 7a | 9.15 |
| 7b | 10.13 |
| 8 | 9.68 |
| 9 | 9.93 |
| 10 | 9.94 |
| 12 | 9.91 |
| 14 | 10.00 |
| 15 | 10.34 |
| 16 | 10.36 |
| 19 | 9.38 |

The ability of the compounds of the invention to penetrate the central nervous system and to bind at the nk1 receptor may be determined using the gerbil foot tapping model as described by Rupniak & Williams, Eur. Jour. of Pharmacol., 1994.

The compound was orally administered and four hours later an NK1 agonist (e.g. delta-Aminovaleryl$^6$[Pro$^9$,Me-Leu$^{10}$]-substance P (7-11)) (3 pmol in 5 μL icv) was infused directly in the cerebral ventricules of the animals. The duration of hind foot tapping induced by the NK1 agonist (e.g. delta-Aminovaleryl$^6$[Pro$^9$,Me-Leu$^{10}$]-substance P (7-11)) was recorded continuously for 3 min using a stopclock. The dose of the test compound required to inhibit by 50% the tapping induced by the NK1 agonist (e.g. delta-Aminovaleryl$^6$[Pro$^9$,Me-Leu$^{10}$]-substance P (7-11)) expressed as mg/kg is referred as the $ED_{50}$ values. Alternatively the compounds may be administered subcutaneously or intraperitoneally.

Representative results obtained for compounds of the invention when given by oral administration are given in the following table

| Ex N° | $ED_{50\ (mg/kg)}$ |
|---|---|
| 3 | 0.05 |
| 7b | 0.19 |
| 12 | 0.27 |

Examples Nos 47, 49 and 52 described in WO 97/16440 have shown in the gerbil foot tapping model no ability up to 1 mg/Kg to penetrate the central nervous system when orally administered 4 hours before the administration of an NK1 agonist (e.g. delta-Aminovaleryl$^6$-[Pro$^9$,Me-Leu$^{10}$]-substance P (7-11)) (3 pmol in 5 μL icv).

No untoward effects have been observed when compounds of the invention have been administered to the gerbil at the pharmacological active doses.

The invention claimed is:
1. A compound of formula (I)

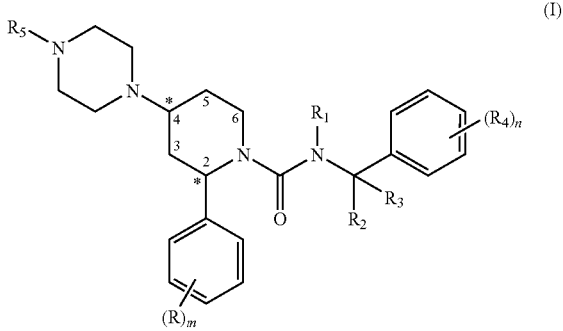

wherein
m is 2
one R is at the 2 position and is methyl and one R is at the 4 position and is fluoro;
n is 2;
both $R_4$ are trifluoromethyl and are at the 3 and 5 positions;
$R_1$ is methyl;
$R_2$ is methyl;
$R_3$ is hydrogen; and
$R_5$ is $C(O)CH_3$;
or a pharmaceutically acceptable salt thereof.

2. 4-(S)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide or a pharmaceutically acceptable salt thereof.

3. 4-(S)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide.

4. The compound according to claim 1 in amorphous form.
5. The compound according to claim 1 in crystalline form.
6. The compound according to claim 2 in amorphous form.
7. The compound according to claim 2 in crystalline form.
8. The compound according to claim 3 in amorphous form.
9. The compound according to claim 3 in crystalline form.
10. A pharmaceutical composition comprising the compound according to claim 1 and one or more pharmaceutically acceptable carriers or excipients.

11. A pharmaceutical composition comprising the compound according to claim 2 and one or more pharmaceutically acceptable carriers or excipients.

12. A pharmaceutical composition comprising the compound according to claim 3 and one or more pharmaceutically acceptable carriers or excipients.

13. The pharmaceutical composition according to claim 10 further comprising a 5HT3 antagonist selected from the group consisting of ondansetron, granisetron and metoclopramide.

14. The pharmaceutical composition according to claim 11 further comprising a 5HT3 antagonist selected from the group consisting of ondansetron, granisetron and metoclopramide.

15. The pharmaceutical composition according to claim 12 further comprising a 5HT3 antagonist selected from the group consisting of ondansetron, granisetron and metoclopramide.

16. A method for the treatment of emesis in a mammal in need thereof comprising administering to said mammal an effective amount of the compound according to claim 1.

17. A method for the treatment of emesis in a mammal in need thereof comprising administering to said mammal an effective amount of the compound according to claim 2.

18. A method for the treatment of emesis in a mammal in need thereof comprising administering to said mammal an effective amount of the compound according to claim 3.

19. The method according to claim 6, wherein said mammal is man.

20. The method according to claim 17, wherein said mammal is man.

21. The method according to claim 18, wherein said mammal is man.

22. The method according to claim 6, wherein said emesis is delayed emesis.

23. The method according to claim 17, wherein said emesis is delayed emesis.

24. The method according to claim 18, wherein said emesis is delayed emesis.

25. The method according to claim 6, wherein said emesis is anticipatory emesis.

26. The method according to claim 17, wherein said emesis is anticipatory emesis.

27. The method according to claim 18, wherein said emesis is anticipatory emesis.

28. The method according to claim 6, wherein said emesis is induced by cancer chemotherapeutic agents.

29. The method according to claim 17, wherein said emesis is induced by cancer chemotherapeutic agents.

30. The method according to claim 18, wherein said emesis is induced by cancer chemotherapeutic agents.

31. The method according to claim 28, wherein said cancer chemotherapeutic agent is selected from the group consisting of cyclophosphamide, carmustine, lomustine, chlorambucil, dactinomycin, doxorubicin, mitomycin-C, bleomyci n, cytarabine, methotrexate, 5-fluorouracil, etoposide, vinblastine, vincristine, cisplatin, dacarbazine, procarbazine and hydroyurea.

32. The method according to claim 29, wherein said cancer chemotherapeutic agent is selected from the group consisting of cyclophosphamide, carmustine, lomustine, chlorambucil, dactinomycin, doxorubicin, mitomycin-C, bleomycin, cytarabine, methotrexate, 5-fluorouracil, etoposide, vinblastine, vincristine, cisplatin, dacarbazine, procarbazine and hydroyurea.

33. The method according to claim 30, wherein said cancer chemotherapeutic agent is selected from the group consisting of cyclophosphamide, carmustine, lomustine, chlorambucil, dactinomycin, doxorubicin, mitomycin-C, bleomyci n, cytarabine, methotrexate, 5-fluorouracil, etoposide, vinblastine, vincristine, cisplatin, dacarbazine, procarbazine and hydroyurea.

34. The method according to claim 16, wherein said emesis is induced by radiation sickness or radiation therapy.

35. The method according to claim 17, wherein said emesis is induced by radiation sickness or radiation therapy.

36. The method according to claim 18, wherein said emesis is induced by radiation sickness or radiation therapy.

37. The method according to claim 16, wherein said emesis is induced by pregnancy.

38. The method according to claim 17, wherein said emesis is induced by pregnancy.

39. The method according to claim 18, wherein said emesis is induced by pregnancy.

40. The method according to claim 16, wherein said emesis is induced by post-operative sickness.

41. The method according to claim 17, wherein said emesis is induced by post-operative sickness.

42. The method according to claim 18, wherein said emesis is induced by post-operative sickness.

43. The method according to claim 16, wherein said emesis is induced by migraine.

44. The method according to claim 17, wherein said emesis is induced by migraine.

45. The method according to claim 18, wherein said emesis is induced by migraine.

46. The method according to claim 16, wherein said emesis is induced by opiod analgesics.

47. The method according to claim 17, wherein said emesis is induced by opiod analgesics.

48. The method according to claim 18, wherein said emesis is induced by opiod analgesics.

49. The method according to claim 16, further comprising administering an effective amount of a 5HT3 antagonist.

50. The method according to claim 17, further comprising administering an effective amount of a 5HT3 antagonist.

51. The method according to claim 18, further comprising administering an effective amount of a 5HT3 antagonist.

52. The method according to claim 49, wherein said 5HT3 antagonist is selected from the group consisting of ondansetron, granisetron and metoclopramide.

53. The method according to claim 50, wherein said 5HT3 antagonist is selected from the group consisting of ondansetron, granisetron and metoclopramide.

54. The method according to claim 51, wherein said 5HT3 antagonist is selected from the group consisting of ondansetron, granisetron and metoclopramide.

55. The method according to claim 16, further comprising administering an effective amount of ondansetron.

56. The method according to claim 17, further comprising administering an effective amount of ondansetron.

57. The method according to claim 18, further comprising administering an effective amount of ondansetron.

58. A method for the treatment of emesis in a mammal being treated with an opiod analgesic, said method comprising administering to said mammal an effective amount of the compound according to claim 1.

59. The method according to claim 58, wherein said compound is 4-(S)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide or a pharmaceutically acceptable salt thereof.

60. The method according to claim 58, wherein said compound is 4-(S)-(4-acetyl-piperazin-1-yl)-2-(R)-(4-fluoro-2- methyl-phenyl)-piperidine-1-carboxylic acid, [1-(R)-(3,5-bis-trifluoromethyl-phenyl)-ethyl]-methylamide.

61. A method for the treatment of emesis in a mammal being treated with an opiod analgesic, said method comprising administering to said mammal an effective amount of 4-(S)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide methanesulphonate.

62. The method according to claim 58, wherein said compound is administered prior to, during, or after treatment with said opiod analgesic.

63. The method according to claim 61, wherein said compound is administered prior to, during, or after treatment with said opiod analgesic.

64. The method according to claim 58, wherein said mammal is man.

65. The method according to claim 61, wherein said mammal is man.

66. The method according to claim 58, wherein said opiod analgesic is morphine.

67. The method according to claim 61, wherein said opiod analgesic is morphine.

* * * * *